US012569179B2

(12) United States Patent
Nakamura et al.

(10) Patent No.: US 12,569,179 B2
(45) Date of Patent: Mar. 10, 2026

(54) BIOLOGICAL INFORMATION ACQUISITION SYSTEM AND ELECTRODE SHEET

(71) Applicants: HOSEI UNIVERSITY, Tokyo (JP); MEKTEC CORPORATION, Tokyo (JP)

(72) Inventors: Sousuke Nakamura, Tokyo (JP); Masayuki Iwase, Tokyo (JP)

(73) Assignees: HOSEI UNIVERSITY, Tokyo (JP); MEKTEC CORPORATION, Tokyo (JP)

( * ) Notice: Subject to any disclaimer, the term of this patent is extended or adjusted under 35 U.S.C. 154(b) by 269 days.

(21) Appl. No.: 18/256,008

(22) PCT Filed: Oct. 14, 2022

(86) PCT No.: PCT/JP2022/038337
§ 371 (c)(1),
(2) Date: Jun. 5, 2023

(87) PCT Pub. No.: WO2023/181466
PCT Pub. Date: Sep. 28, 2023

(65) Prior Publication Data
US 2024/0366136 A1 Nov. 7, 2024

(30) Foreign Application Priority Data
Mar. 22, 2022 (JP) ................................. 2022-045527

(51) Int. Cl.
*A61B 5/282* (2021.01)
*A61B 5/00* (2006.01)
(Continued)

(52) U.S. Cl.
CPC ............ *A61B 5/282* (2021.01); *A61B 5/1116* (2013.01); *A61B 5/26* (2021.01); *A61B 5/277* (2021.01);
(Continued)

(58) Field of Classification Search
CPC ........... A61B 5/277; A61B 5/28; A61B 5/282; A61B 5/304; A61B 5/6892;
(Continued)

(56) References Cited

U.S. PATENT DOCUMENTS 8,634,901 B2 * 1/2014 Callahan ................ A61B 5/318
607/9
2019/0029595 A1 1/2019 Sekitani et al.
(Continued)

FOREIGN PATENT DOCUMENTS

JP 2010-012161 A 1/2010
JP 2010051359 A * 3/2010
(Continued)

OTHER PUBLICATIONS

S. Nakamura et al., "Capacitively Coupled Electrode Array Sensors for Body Posture and ECG Measurement During Sleep", vol. 9, p. 24363-24372, 2021, IEEE Access/2021.3057256.
(Continued)

*Primary Examiner* — Eun Hwa Kim
(74) *Attorney, Agent, or Firm* — Studebaker Brackett PLLC

(57) ABSTRACT

Provided is a biological information acquisition system capable of acquiring an electric parameter and biological information that are more accurate. A biological information acquisition system 200 includes a flexible electrode sheet 100 having multiple electrodes 30 arranged in an array, an electrode selector that acquires an electric parameter from the multiple electrodes 30 in a state in which the electrode sheet 100 is arranged along a biological body 300 such that the multiple electrodes 30 do not contact the biological body 300 to select the electrodes 30 to be used for acquisition of biological information based on the acquired electric parameter, and a biological information acquirer that acquires the (Continued)

100 biological information from the electrodes 30 selected by the electrode selector in a state in which the electrode sheet 100 is arranged along the biological body 300 such that the multiple electrodes 30 do not contact the biological body 300.

9 Claims, 21 Drawing Sheets

(51) Int. Cl.

| | | |
|---|---|---|
| *A61B 5/11* | (2006.01) | |
| *A61B 5/26* | (2021.01) | |
| *A61B 5/277* | (2021.01) | |
| *A61B 5/304* | (2021.01) | |

(52) U.S. Cl.
CPC .......... *A61B 5/7267* (2013.01); *A61B 5/6887* (2013.01); *A61B 2560/0468* (2013.01); *A61B 2562/0214* (2013.01); *A61B 2562/046* (2013.01); *A61B 2562/164* (2013.01); *A61B 2562/227* (2013.01)

(58) Field of Classification Search
CPC .... A61B 2562/0468; A61B 2562/0214; A61B 2562/046; A61B 2562/164; A61B 2562/277

See application file for complete search history.

(56) References Cited

U.S. PATENT DOCUMENTS

| | | |
|---|---|---|
| 2019/0192024 A1 | 6/2019 | Watson et al. |
| 2022/0202334 A1* | 6/2022 | Batzer .................... G16H 30/20 |

FOREIGN PATENT DOCUMENTS

| | | |
|---|---|---|
| JP | 2020-120765 A | 8/2020 |
| JP | 2021-016404 A | 2/2021 |
| JP | 2021-074627 A | 5/2021 |
| JP | 2021-094147 A | 6/2021 |

OTHER PUBLICATIONS

International Search Report issued in PCT/JP2022/038337; mailed Nov. 22, 2022.
An Office Action, "Notice of Reasons for Refusal," mailed by the Japanese Patent Office on Dec. 2, 2025, in Japanese Patent Application No. 2022-045527; with English language translation.

* cited by examiner

BIOLOGICAL INFORMATION ACQUISITION SYSTEM AND ELECTRODE SHEET

TECHNICAL FIELD

The present invention relates to a biological information acquisition system and an electrode sheet.

BACKGROUND ART

A biological information acquisition system that acquires a biological signal from a biological body with capacitively-coupled electrodes in a state in which an insulator is interposed between the electrodes and the biological body may include, for example, one described in Non-Patent Literature 1. The biological information acquisition system of Non-Patent Literature 1 includes a hard board having multiple electrodes arranged in an array, and the multiple electrodes are exposed to the outside in the board. When the biological signal is acquired, the clothes of a subject (biological body) form the insulator, and the electrode, the clothes (insulator) of the subject, and the skin of the subject form a capacitor.

CITATION LIST

Patent Literature

Non-Patent Literature 1: S. NAKAMURA et al, "Capacitively Coupled Electrode Array Sensors for Body Posture and ECG Measurement During Sleep," vol. 9, p 24363-24372, 2021, IEEE Access/2021.3057256

SUMMARY OF INVENTION

Problems to be Solved by Invention

However, the biological information acquisition system described in Non-Patent Literature 1 still has room for improvement for acquiring a more-accurate electrocardiogram waveform.

The present invention has been made in view of the above-described problems, and provides a biological information acquisition system and an electrode sheet capable of acquiring more-accurate biological information.

Solution to Problems

According to the present invention, there is provided a biological information acquisition system including:
  a flexible electrode sheet having multiple electrodes arranged in an array;
  an electrode selector that acquires an electric parameter from the multiple electrodes in a state in which the electrode sheet is arranged along a biological body such that the multiple electrodes do not contact the biological body to select an electrode to be used for acquisition of biological information based on the acquired electric parameter; and
  a biological information acquirer that acquires the biological information from the electrode selected by the electrode selector in a state in which the electrode sheet is arranged along the biological body such that the multiple electrodes do not contact the biological body.
According to the present invention, there is provided an electrode sheet including:
  multiple unit sheets connected to each other, in which each of the unit sheets has a stretchable base, multiple stretchable lines formed on the stretchable base and extending parallel with each other, and multiple electrodes each formed at one end of two or more of the stretchable lines.
  the multiple unit sheets are arranged in a direction of arrangement of the multiple electrodes, and
  of the stretchable lines of one of the unit sheets, the stretchable lines which do not end at the electrodes are each individually connected to the stretchable lines of another one of the unit sheets adjacent to the one of the unit sheets.

Effects of Invention

According to the present invention, the electrode sheet can be easily arranged in accordance with the uneven body surface of the biological body, and therefore, an electric parameter and biological information that are more accurate can be acquired.

BRIEF DESCRIPTION OF DRAWINGS

Figure 1:
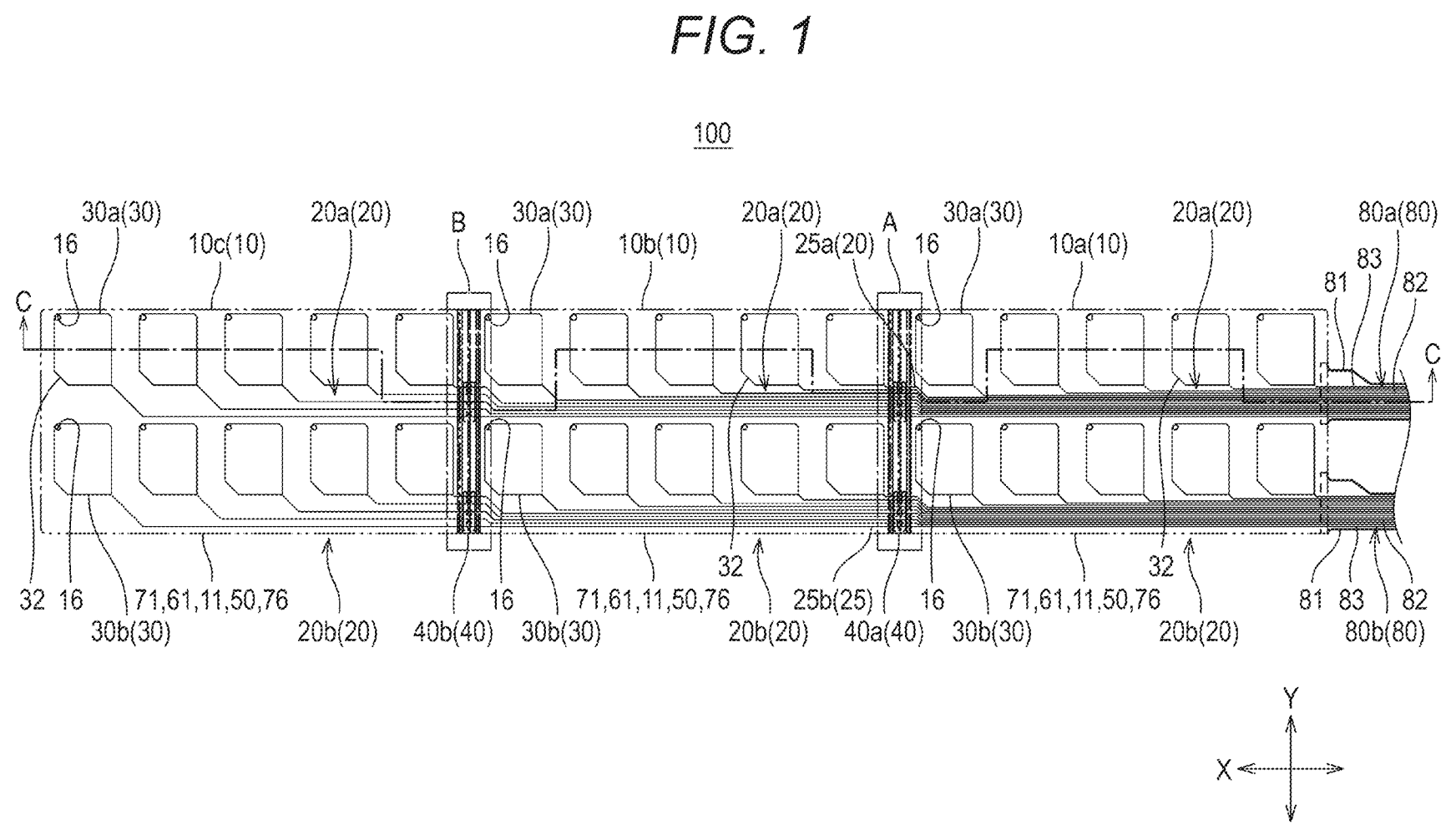

FIG. 1 is a schematic plan view showing an electrode sheet according to a first embodiment;

Figure 2:
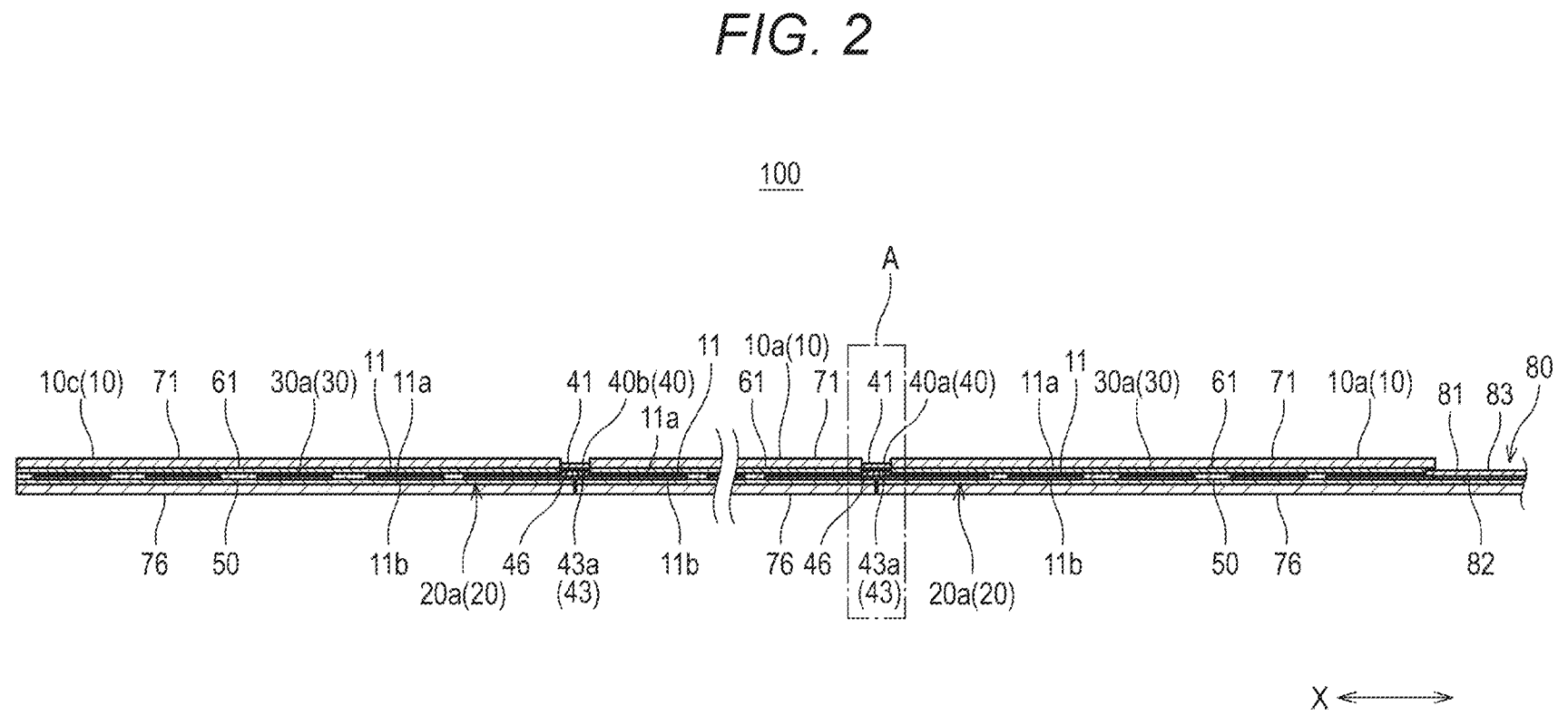

FIG. 2 is a schematic end view showing the electrode sheet according to the first embodiment;

Figure 3:
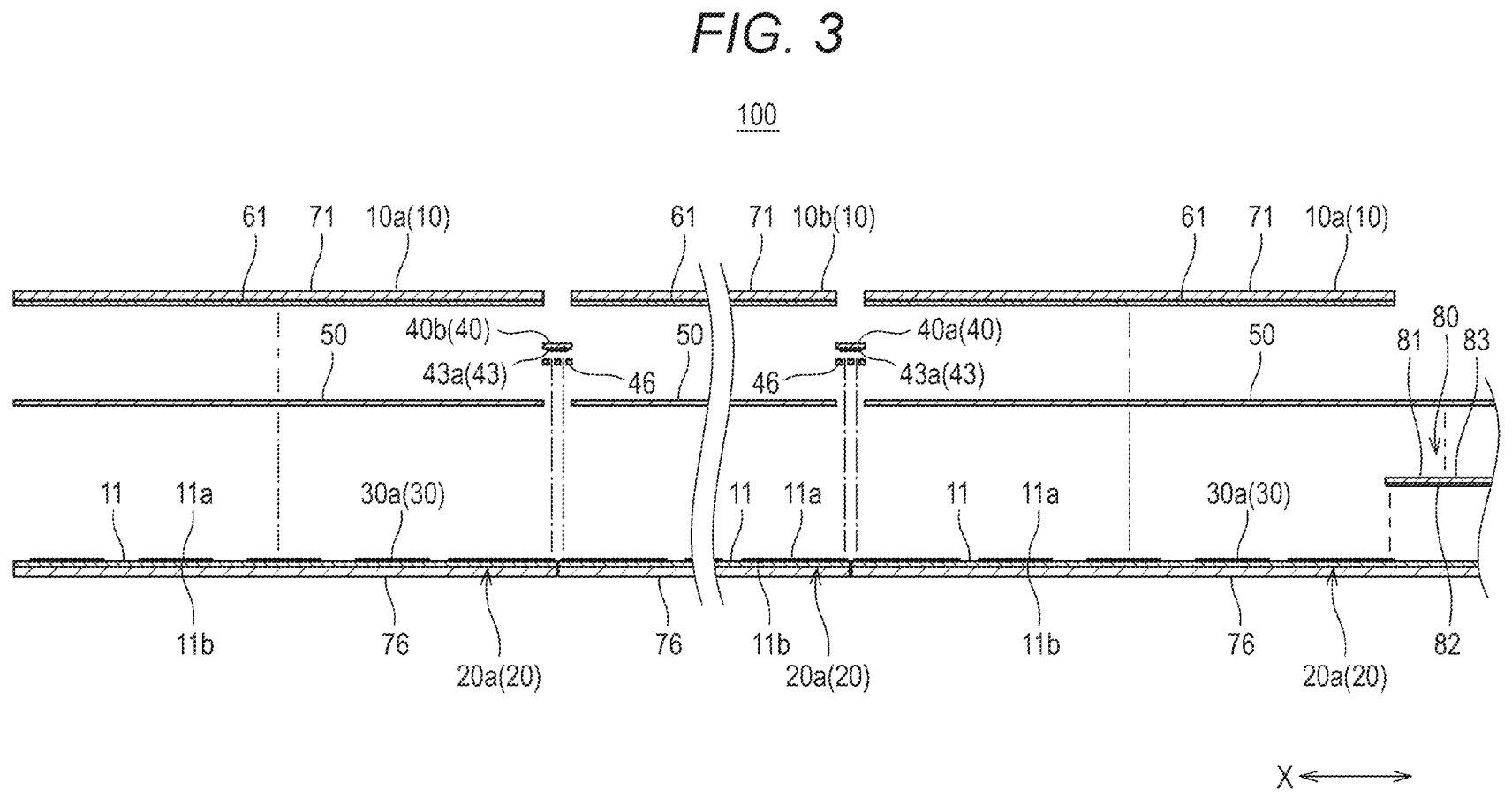

FIG. 3 is a schematic exploded end view showing the electrode sheet according to the first embodiment;

Figure 5:
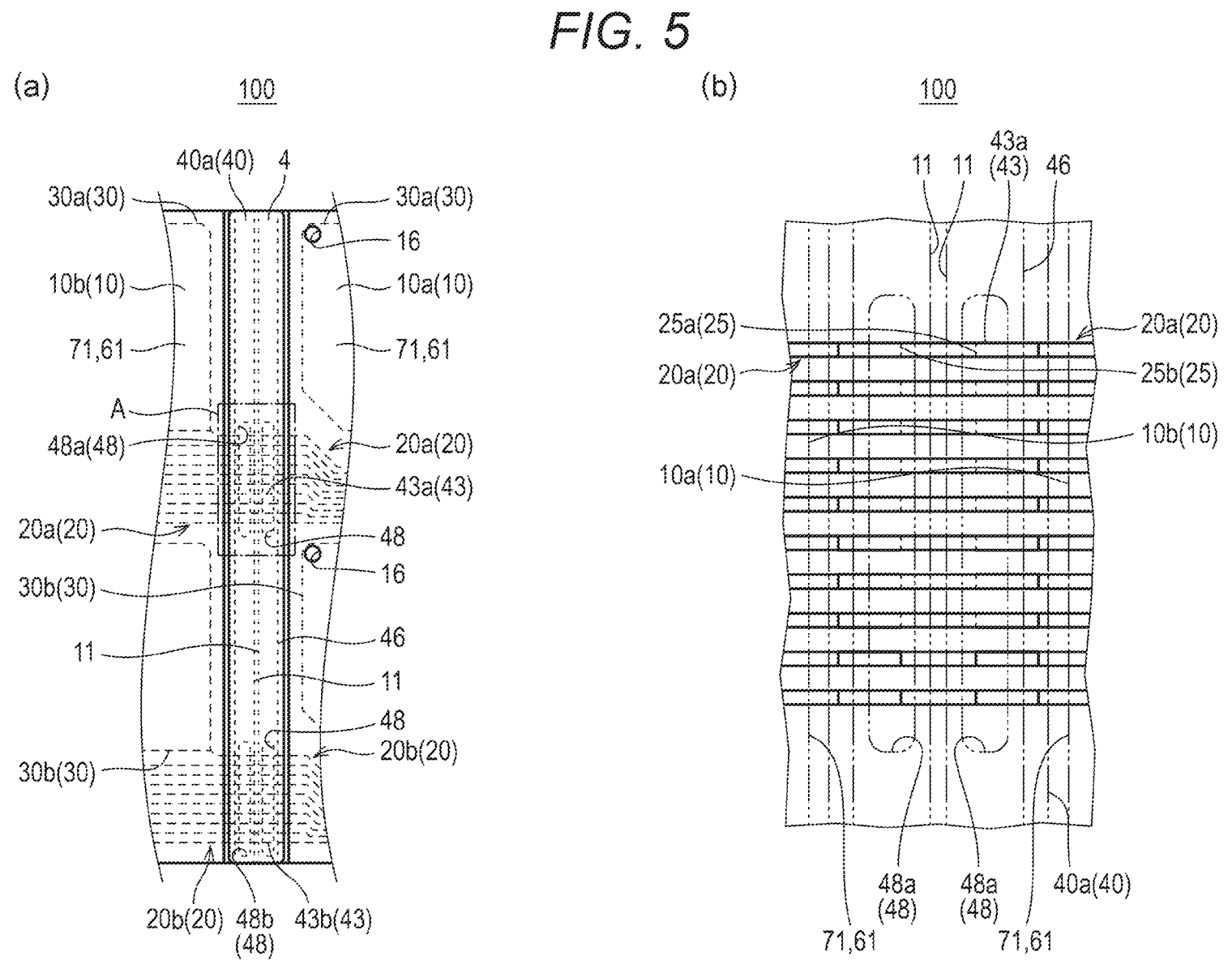

FIG. 5(a) is a partially-enlarged view of a portion A shown in FIG. 1, and FIG. 5(b) is a partially-enlarged view of a portion A shown in FIG. 5(a);

FIG. 6(a) is a partially-enlarged view of a portion B shown in FIG. 1, and FIG. 6(b) is a partially-enlarged view of a portion A shown in FIG. 6(a);

Figure 7:
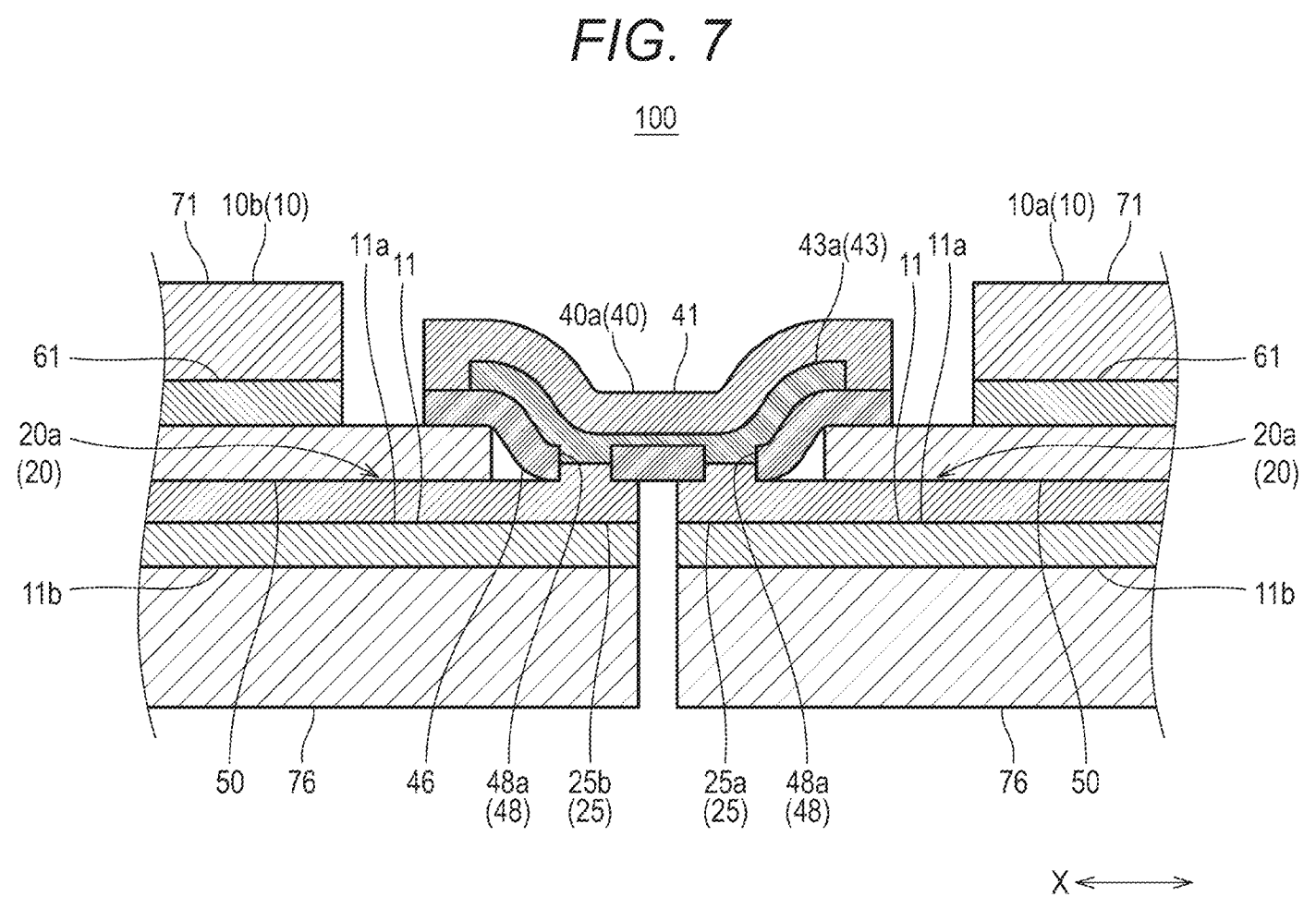

FIG. 7 is a partially-enlarged view of a portion A shown in FIG. 2;

FIG. 12 is a schematic view showing a state in which the electrode sheet unit in the first embodiment is bonded to a sheet;

FIGS. 16(*a*) and 16(*b*) are schematic end views showing an electrode sheet according to a modification of the first embodiment;

FIG. 18 is a schematic exploded end view showing the electrode sheet according to the second embodiment;

DESCRIPTION OF EMBODIMENTS

Figure 4:
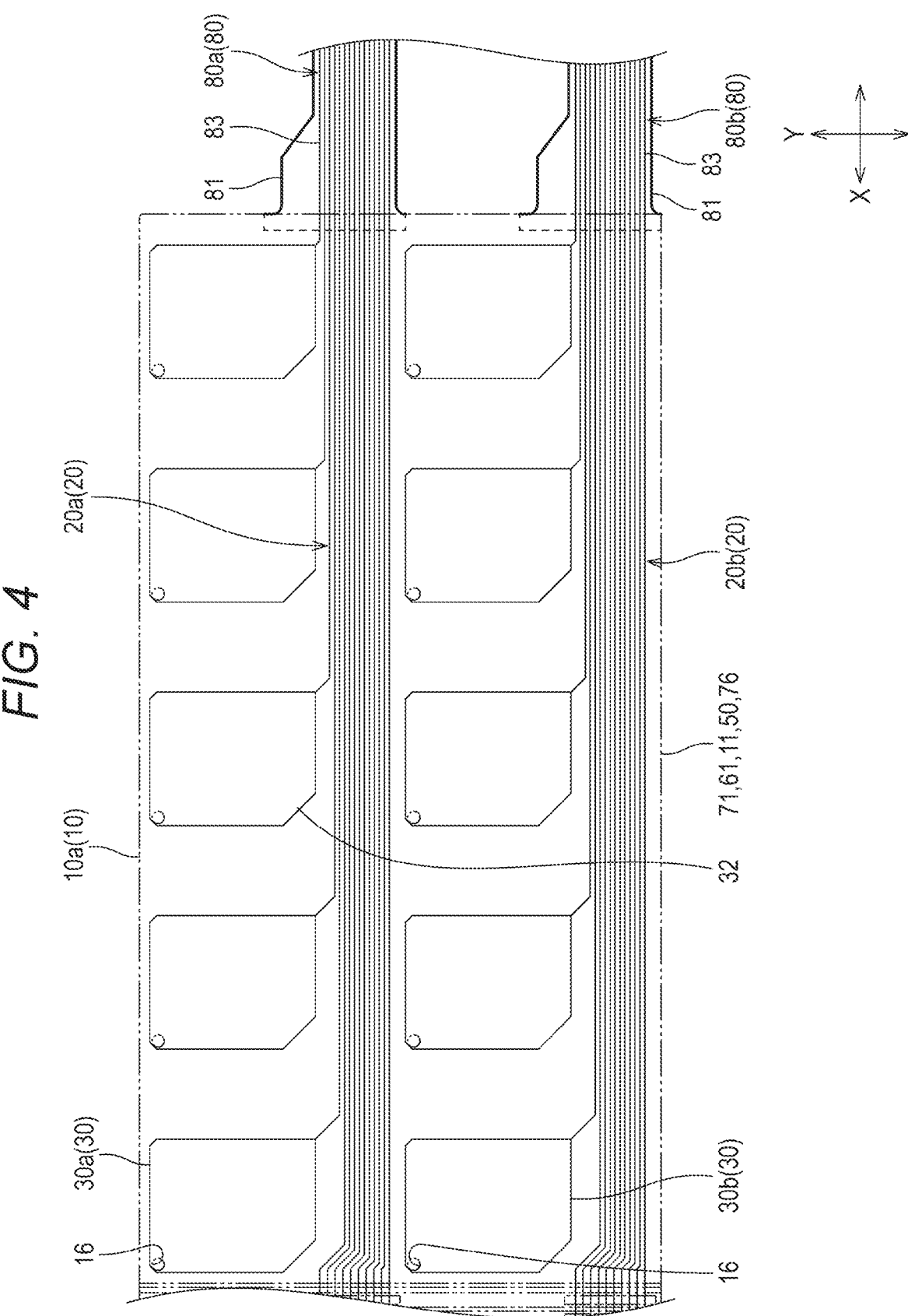
FIG. 4 is a schematic plan view showing a first unit sheet in the first embodiment.

[First Embodiment] Hereinafter, a first embodiment of the present invention will be described using FIGS. 1 to 15(*b*). Note that in all the drawings, the same reference numerals are used to represent similar components and description thereof will be omitted as necessary. FIGS. 2 and 3 show a cut surface of an electrode sheet 100 along a C-C line of FIG. 1. In FIGS. 1 and 4, components other than an electrode 30 and a stretchable line 20 in the electrode sheet 100 are indicated by chain double-dashed lines. In FIGS. 5(*b*) and 6(*b*), components other than the stretchable line 20 and a stretchable junction line 43 are indicated by chain double-dashed lines.

As shown in FIGS. 1 to 3, a biological information acquisition system 200 according to the present embodiment includes a flexible electrode sheet 100 having multiple electrodes 30 arranged in an array.

The biological information acquisition system 200 further includes an electrode selector that acquires an electric parameter from the multiple electrodes 30 in a state in which the electrode sheet 100 is arranged along a biological body 300 such that the multiple electrodes 30 do not contact the biological body 300 (see FIG. 12) to select the electrodes 30 used for acquisition of biological information based on the acquired electric parameter, and a biological information acquirer that acquires the biological information from the electrodes 30 selected by the electrode selector in a state in which the electrode sheet 100 is arranged along the biological body 300 such that the multiple electrodes 30 do not contact the biological body 300.

Note that the phrase "select the electrodes 30" herein means that "only some of the multiple electrodes 30 are selected," and does not mean that "all the multiple electrodes 30 are selected."

Figure 8:
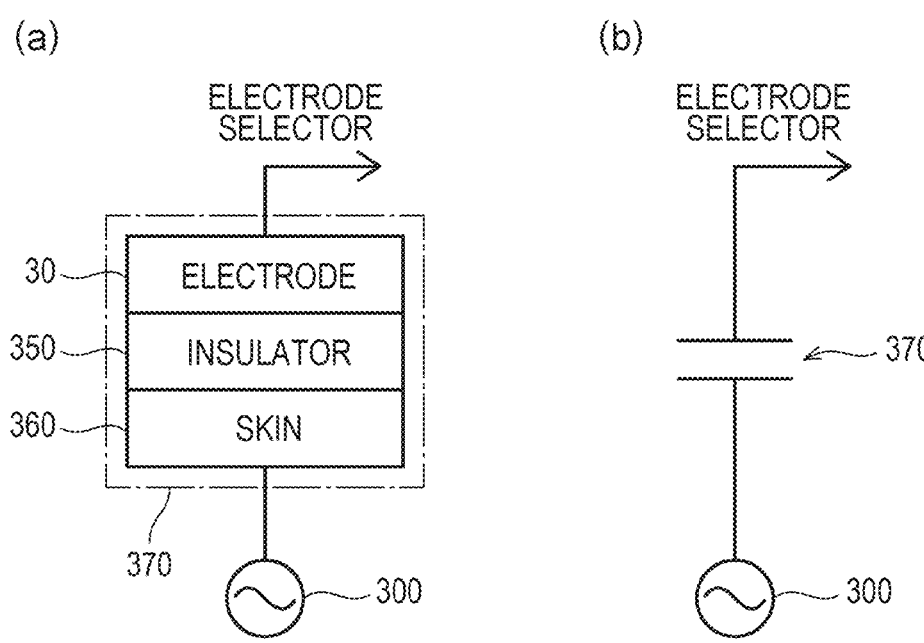
FIGS. 8(a) and 8(b) are diagrams for describing a capacitively-coupled electrode in the first embodiment.

In the biological information acquisition system 200, the biological information is acquired in a state in which an insulator 350 (e.g., clothes) is interposed between the multiple electrodes 30 and the biological body 300 (e.g., a skin 360). That is, the biological information acquisition system 200 acquires the biological information with capacitively-coupled electrodes. More specifically, as shown in FIGS. 8(*a*) and 8(*b*), the electrode 30, the insulator 350, and the skin 36) form a capacitor 370, and therefore, the biological information acquirer can acquire an electric signal from the biological body 300. The biological information acquirer can acquire the biological information such as an electrocardiogram waveform, a heart rate, and a respiration based on the acquired electric signal.

Moreover, since the multiple electrodes 30, the insulator 350, and the skin 360 form the capacitors 370, an electrostatic capacitance accumulated in each electrode 30 can also be acquired (measured) (details will be described later), for example.

For acquiring an electric parameter and biological information that are more accurate, ones of the multiple electrodes 30 arranged at positions corresponding to the biological body 300 are preferably arranged in accordance with an uneven body surface of the biological body 300.

According to the present embodiment, since the electrode sheet 100 having the multiple electrodes 30 is flexible, the electrode sheet 100 is stretchable and curvable in accordance with the uneven body surface of the biological body 300.

Thus, as compared to a case where the multiple electrodes 30 are formed on a hard board, ones, which are arranged at the positions corresponding to the biological body 300, of the multiple electrodes 30 included in the electrode sheet 100 are easily arranged in accordance with the uneven body surface of the biological body 300. As a result, the capacitance of the capacitor 370 formed by the electrode 30, the insulator 350, and the skin 360 can be stably ensured, and therefore, an electric parameter and biological information that are more accurate can be acquired.

Moreover, since the electrode sheet 100 is flexible, the flexibility and moisture permeability of the electrode sheet 100 can be sufficiently ensured.

Thus, the less-invasive electrode sheet 100 and therefore the less-invasive biological information acquisition system 2(*x*) can be achieved with a comfortable feeling of use.

First, the electrode sheet 100 of the biological information acquisition system 200 will be described in more detail.

Hereinafter, in description of, inter alia, a positional relationship between the components of the electrode sheet 100, the upper side in FIG. 2 will be referred to as an upper side or above, and the opposite side thereof will be referred to as a lower side or below, for example. Moreover, the left side in FIG. 2 will be referred to as a left side or a left, and the opposite side thereof will be referred to as a right side or a right, for example. However, these directions are defined for the sake of convenience, and do not limit the directions of the electrode sheet 100 upon manufacturing and use.

The right-left direction in FIGS. 1 to 3 will be referred to as an X-direction, and the up-down direction in FIG. 1 will be referred to as a Y-direction. The X-direction and the Y-direction are directions (horizontal directions) parallel with the direction of the plane of the electrode sheet 100, and are perpendicular to the up-down direction (direction perpendicular to the plane of the electrode sheet 100) in FIG. 2.

As shown in FIG. 1, the electrode sheet 100 includes, for example, multiple unit sheets 10 connected to each other.

As compared to a case where the electrode sheet 100 is a single sheet material, each unit sheet 10 can be formed with relatively-smaller dimensions, and therefore, can be manufactured with a favorable yield rate. Further, the multiple unit sheets 10 are connected to each other to form the single electrode sheet 100 after non-defective ones of the multiple unit sheets 10 manufactured with the small dimensions have been screened, and therefore, the high-quality electrode sheet 100 with desired dimensions can be easily manufactured. In the case of the present embodiment, the electrode sheet 100 includes, as the unit sheets 10, three unit sheets 10 arranged in the right-left direction (X-direction), as one example.

Hereinafter, these three unit sheets 10 will be referred to as a first unit sheet 10*a*, a second unit sheet 10*b*, and a third unit sheet 10*c* in this order from the right. Each of the unit sheets 10 (first unit sheet 10*a* to third unit sheet 10*c*) is formed in a substantially rectangular shape elongated in the X-direction as viewed in plane, for example. That is, the longitudinal direction of each unit sheet 10 is coincident with the direction of arrangement of the unit sheets 10.

Note that in the present invention, the number of unit sheets 10 included in the electrode sheet 100 is not specifically limited and is settable as necessary according to, e.g., the use of the electrode sheet 100 and the shape and outer dimensions of a target to which the electrode sheet 100 is attached.

Moreover, in the present invention, the electrode sheet 100 does not necessarily include the multiple unit sheets 10, and may include a single sheet material.

As shown in any of FIGS. 1 to 3, each unit sheet 10 is a multilayer body formed in a sheet shape. More specifically, each of the unit sheets 10 (first unit sheet 10a to third unit sheet 10c) includes a stretchable base 11, multiple stretchable lines 20 formed on the stretchable base 11 and extending parallel with each other, multiple electrodes 30 each formed at one end of two or more of the multiple stretchable lines 20, and a stretchable cover 50 covering the multiple stretchable lines 20.

As shown in FIGS. 1, 2, 5(a), and 6(a), in the direction (i.e., X-direction) of arrangement of the unit sheets 10, a gap is formed between one unit sheet 10 and another unit sheet 10 adjacent to the one unit sheet 10, for example. Note that in the present invention, no gap may be formed between adjacent ones of the unit sheets 10.

The gap between the one unit sheet 10 and the another unit sheet 10 adjacent to the one unit sheet 10 is preferably 1.5 mm or less, and in the present embodiment, is 1 mm as one example.

The stretchable base 11 is a thin sheet material stretchable in at least one direction of in-plane directions. Preferably, the stretchable base 11 is stretchable in two directions of in-plane directions. The stretchability of the stretchable base 11 in an in-plane direction may be isotropic, or may be anisotropic, i.e., the stretchability vanes in multiple in-plane directions. Note that the stretchability described herein indicates such properties that tension acts on the stretchable base 11 to stretch the stretchable base 11 and compressive force acts on the stretchable base 11 to contract the stretchable base 11. A change in the dimensions and shape of the stretchable base 11 is greater in stretching than in contraction.

According to this configuration, in a state in which the electrode sheet 100 is arranged along the biological body 300, the stretchable base 11 is stretchable and curvable in accordance with the uneven body surface of the biological body 300. Thus, a gap between the biological body 300 and ones, which are arranged at the positions corresponding to the biological body 300, of the multiple electrodes 30 included in the electrode sheet 100 can be uniform. Consequently, the capacitance of the capacitor 370 formed by the electrode 30, the insulator 350, and the skin 360 can be more stably ensured.

The stretchable base 11 contains thermoplastic resin, for example. The thermoplastic resin is preferably one that exhibits hot-melt properties at 50° C. or more. Moreover, the stretchable base 11 is made, for example, of a material having insulating properties.

Examples of the material forming the stretchable base 11 may include, but not specifically limited to, elastomer materials such as nitrile rubber, latex rubber, and urethane-based elastomer.

The thickness dimension of the stretchable base 11 is, but not specifically limited to, preferably 100 μm or less and more preferably 25 μm or less, for example.

The maximum elongation rate of the stretchable base 11 is preferably 10% or more, more preferably 50% or more, much more preferably 100% or more, and still much more preferably 200% or more. The stretchable base 11 configured as described above can exhibit a maximum elongation rate of 300% or more, for example. The maximum elongation rate of the stretchable base 11 as described herein indicates a maximum elongation rate value at which elastic deformation is possible in one direction of in-plane directions.

Note that in the present embodiment, the elongation rate means the percentage of a dimension when stretched in one direction of in-plane directions by force application with respect to a dimension (hereinafter, an elongation-rate-0% dimension) when no force is applied. For example, an elongation rate of 50% indicates a dimension 1.5 times as great as the elongation-rate-0% dimension, and an elongation rate of 100% indicates a dimension twice as great as the elongation-rate-0% dimension.

As shown in FIGS. 2 and 3, the multiple electrodes 30 are directly formed on one surface 11a of the stretchable base 11, for example.

In the case of the present embodiment, in the electrode sheet 100, the multiple electrodes 30 are arranged in two rows in the Y-direction, and each row includes 15 electrodes 30 arranged in the X-direction, for example. That is, in the electrode sheet 100, 30 electrodes 30 are arranged in two rows and 15 columns in total.

More specifically, in each of the unit sheets 10 (first unit sheet 10a to third unit sheet 10c), the multiple electrodes 30 are arranged in two rows in the Y-direction, and each row includes five electrodes 30 arranged in the X-direction, for example. That is, in each unit sheet 10, 10 electrodes 30 are arranged in two rows and five columns in total.

In description below, each of the multiple electrodes 30 arranged in a row on one side in the Y-direction will be referred to as a first electrode 30a, and each of the multiple electrodes 30 arranged in a row on the other side in the Y-direction will be referred to as a second electrode 30b.

The multiple first electrodes 30a are arranged in line with (linearly) the multiple first electrodes 30a of the adjacent unit sheet 10 in the X-direction, and the multiple second electrodes 30b are arranged in line with (linearly) the multiple second electrodes 30b of the adjacent unit sheet 10 in the X-direction.

The electrodes 30 have, for example, the same shape and dimensions.

Each electrode 30 is formed, for example, in a substantially rectangular shape slightly elongated in the Y-direction as viewed in plane.

Note that in the present invention, the number of electrodes 30 included in each unit sheet 10 is not specifically limited and is settable as necessary according to, e.g., the use of the electrode sheet 100 and the shape and outer dimensions of the target to which the electrode sheet 100 is attached.

Each of the multiple electrodes 30 has, as one example, a dimension of 40 mm in the X-direction and a dimension of 50 mm in the Y-direction.

The multiple electrodes 30 are separated from each other in the X-direction, and are arranged at equal intervals. An interval between adjacent ones of the electrodes 30 in the X-direction is, for example, preferably 10 mm or more and 30 mm or less, and in the case of the present embodiment, is 20 mm as one example.

Similarly, the multiple electrodes 30 are separated from each other in the Y-direction. An interval between adjacent ones of the electrodes 30 in the Y-direction is, for example, preferably 10 mm or more and 30 mm or less, and in the case of the present embodiment, 20 mm as one example.

According to this configuration, interference between adjacent ones of the electrodes 30 in the unit sheet 10 can be reduced.

Note that in the present invention, the interval between adjacent ones of the electrodes 30 is not limited to this example.

As shown in FIGS. 1 and 4, in the case of the present embodiment, a separation distance between the upper edge of each first electrode 30*a* and the upper edge of the electrode sheet 100 in the Y-direction is less than a separation distance between the lower edge of each second electrode 30*b* and the lower edge of the electrode sheet 100 in the Y-direction.

With this configuration, in a state in which multiple electrode sheets 100 are arranged close to each other in the Y-direction as described later (see FIG. 11), the multiple electrodes 30 can be arranged at equal intervals in the Y-direction.

As shown in FIGS. 2 and 3, the multiple stretchable lines 20 are directly formed on one surface 11*a* of the stretchable base 11, for example. Each stretchable line 20 extends in the X-direction, for example. More specifically, each stretchable line 20 includes, for example, a portion extending in the X-direction and a portion upwardly inclined as described later, but extends substantially in the X-direction as a whole.

Each of the unit sheets 10 (first unit sheet 10*a* to third unit sheet 10*c*) includes, as the multiple stretchable lines 20, multiple first stretchable lines 20*a* and multiple second stretchable lines 20*b*.

Each of the multiple first stretchable lines 20*a* is arranged, for example, on the other side (lower side in FIGS. 1 and 4) with respect to the multiple first electrodes 30*a* in the Y-direction.

Similarly, each of the multiple second stretchable lines 20*b* is arranged, for example, on the other side (lower side in FIGS. 1 and 4) with respect to the multiple second electrodes 30*b* in the Y-direction.

In one unit sheet 10, the first electrodes 30*a* are each formed at one end of two or more of the multiple first stretchable lines 20*a*. That is, two or more first stretchable lines 20*a* end at the first electrodes 30*a*. On the other hand, each of the remaining first stretchable lines 20*a* which do not end at the first electrodes 30*a* extends from the left end to the right end of the stretchable base 11, as one example.

Similarly, in one unit sheet 10, the second electrodes 30*b* are each formed at one end of two or more of the multiple second stretchable lines 20*b*. That is, two or more second stretchable lines 20*b* end at the second electrodes 30*b*. On the other hand, each of the remaining second stretchable lines 20*b* which do not end at the second electrodes 30*b* extends from the left end to the right end of the stretchable base 11, as one example.

Note that as described later, in the third unit sheet 10*c*, all the first stretchable lines 20*a* end at the first electrodes 30*a* and there are no first stretchable lines 20*a* which do not end at the first electrodes 30*a*. Similarly, in the third unit sheet 10*c*, all the second stretchable lines 20*b* end at the second electrodes 30*b*, and there are no second stretchable lines 20*b* which do not end at the second electrodes 30*b*.

The stretchable cover 50 is arranged and stacked on one surface 11*a* of the stretchable base 11, for example.

The stretchable cover 50 covers each of the multiple stretchable lines 20 and the multiple electrodes 30. More specifically, the lower surface of the stretchable cover 50 is substantially entirely in direct contact with the upper surface (one surface 11*a*) of the stretchable base 11, except for each of regions formed with the stretchable lines 20 and the electrodes 30.

The stretchable cover 50 contains thermoplastic resin as does the stretchable base 11.

Moreover, a material forming the stretchable cover 50 is, but not specifically limited to, an elastomer material similar to that of the stretchable base 11, and has insulating properties and stretchability, for example.

Note that the stretchable cover 50 is sufficient when made of at least the material having the insulating properties and the stretchability and may be made of a material different from that of the stretchable base 11.

For example, the thickness dimension of the stretchable cover 50 is, but not specifically limited to, preferably 100 µm or less and more preferably 25 µm or less, for sufficiently ensuring the stretchability of the electrode sheet 100.

As shown in FIGS. 5(*a*), 6(*b*), and 7, end portions of the multiple stretchable lines 20 on a side close to an adjacent one of the unit sheets 10 are exposed through the stretchable cover 50, and form connection terminal portions 25 (below-mentioned first connection terminal portions 25*a* to fourth connection terminal portions 25*d*) connected to the stretchable lines 20 of the another unit sheet 10 adjacent to the one unit sheet 10.

More specifically, as shown in, e.g., FIGS. 1 and 4, each of the stretchable base 11 and the stretchable cover 50 is formed in a substantially rectangular shape elongated in the X-direction. Note that in the X-direction, the length dimension of the stretchable cover 50 is less than the length dimension of the stretchable base 11.

In the first unit sheet 10*a*, each of left end portions of ones (stretchable lines 20 which do not end at the electrodes 30), which extend to the left edge of the stretchable base 11, of the multiple stretchable lines 20 is exposed through the left end of the stretchable cover 50, and forms the first connection terminal portion 25*a* (see FIGS. 5(*b*) and 7) connected to the stretchable line 20 of the second unit sheet 10*b*.

In the second unit sheet 10*b*, each of right end portions of the stretchable lines 20 is exposed through the right end of the stretchable cover 50, and forms the second connection terminal portion 25*b* (FIGS. 5(*b*) and 7) connected to the stretchable line 20 of the first unit sheet 10*a*. Moreover, in the second unit sheet 10*b*, each of left end portions of ones (same as above), which extend to the left edge of the stretchable base 11, of the multiple stretchable lines 20 is exposed through the left end of the stretchable cover 50, and forms the third connection terminal portions 25*c* (see FIG. 6(*c*)) connected to the stretchable line 20 of the third unit sheet 10*c*.

Figure 6:
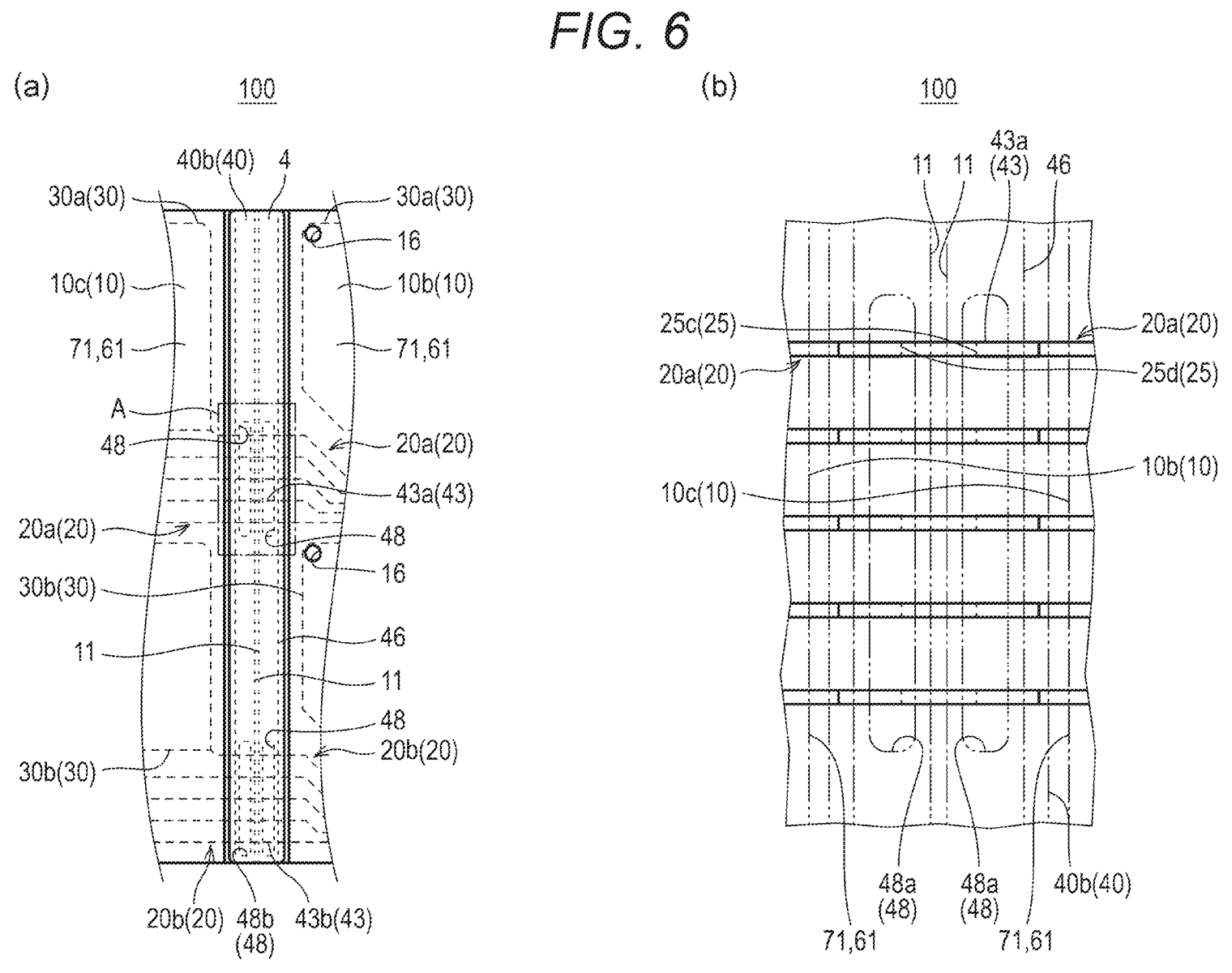

In the third unit sheet 10*c*, each of right end portions of the stretchable lines 20 is exposed through the right end of the stretchable cover 50, and forms the fourth connection terminal portion 25*d* (see FIG. 6(*b*)) connected to the stretchable line 20 of the second unit sheet 10*b*.

The number of first connection terminal portions 25*a* included in the first unit sheet 10*a* is the same as the number of second connection terminal portions 25*b* included in the second unit sheet 10*b*, and the second connection terminal portions 25*b* are connected to the first connection terminal portions 25*a* in one-to-one correspondence. Similarly, the number of third connection terminal portions 25*c* included in the second unit sheet 10*b* is the same as the number of fourth connection terminal portions 25*d* included in the third unit sheet 10*c*, and the fourth connection terminal portions 25*d* are connected to the third connection terminal portions 25*c* in one-to-one correspondence.

As shown in FIG. 5(*b*), each of the first connection terminal portions 25*a* is arranged on an extension of the corresponding second connection terminal portion 25*b*, and is connected to the second connection terminal portion 25*b* via the later-described stretchable junction line 43. Similarly, each of the third connection terminal portions 25*c* is arranged on an extension of the corresponding third connection terminal portion 25*c*, and is connected to the fourth connection terminal portion 25*d* via the later-described stretchable junction line 43.

In the case of the present embodiment, the number of stretchable lines 20 (first stretchable lines 20*a* and second stretchable lines 20*b*) included in each unit sheet 10 decreases in the order of the first unit sheet 10*a*, the second unit sheet 10*b*, and the third unit sheet 10*c*.

More specifically, in the first unit sheet 10*a*, 15 first stretchable lines 20*a* are formed, for example. Of these first stretchable lines 20*a*, five first stretchable lines 20*a* are formed, at the left ends thereof, with the first electrodes 30*a* one by one. Each of the left end portions of the remaining (10) of the multiple first stretchable lines 20*a* forms the first connection terminal portion 25*a*. Similarly, in the first unit sheet 10*a*, 15 second stretchable lines 20*b* are formed, for example. Of these second stretchable lines 20*b*, five second stretchable lines 20*b* are formed, at the left ends thereof, with the second electrodes 30*b* one by one. Each of the left end portions of the remaining (10) of the multiple second stretchable lines 20*b* forms the first connection terminal portions 25*a*.

In the second unit sheet 10*b*, 10 first stretchable lines 20*a* are formed, for example. Of these first stretchable lines 20*a*, five first stretchable lines 20*a* are formed, at the left ends thereof, with the first electrodes 30*a* one by one. Each of the left end portions of the remaining (five) of the multiple first stretchable lines 20*a* forms the third connection terminal portion 25*c*. Similarly, in the second unit sheet 10*b*, 10 second stretchable lines 20*b* are formed, for example. Of these second stretchable lines 20*b*, five second stretchable lines 20*b* are formed, at the left ends thereof, with the second electrodes 30*b* one by one. Of the remaining (five) of the multiple second stretchable lines 20*b*, each of the right end portion forms the second connection terminal portion 25*b*, and each of the left end portion forms the third connection terminal portion 25*c*.

In the third unit sheet 10*c*, five first stretchable lines 20*a* are formed, for example. These five first stretchable lines 20*a* are formed, at the left ends thereof, with the first electrodes 30*a* one by one. Similarly, in the third unit sheet 10*c*, five second stretchable lines 20*b* are formed, for example. These five second stretchable lines 20*b* are formed, at the left ends thereof, with the second electrode 30*b* one by one. That is, in the third unit sheet 10*c*, the first stretchable lines 20*a* which do not end at the first electrode 30*a* and the second stretchable lines 20*b* which do not end at the second electrode 30*b* are not formed.

As described above, the multiple unit sheets 10 are arranged in the direction (X-direction in the case of the present embodiment) of arrangement of the multiple electrodes 30, and ones, which do not end at the electrodes 30, of the stretchable lines 20 of one unit sheet 10 are individually connected to the stretchable lines 20 of another unit sheet 10 adjacent to the one unit sheet 10, for example.

Note that in a case where the multiple electrodes 30 are arranged not only in the Y-direction (rows) but also in the X-direction (columns) as in the present embodiment, the "direction of arrangement of the multiple electrodes 30" means the direction of arrangement of the rows or columns which are greater in number.

As described above, each unit sheet 10 is formed in the substantially rectangular shape elongated in the X-direction. Thus, the longitudinal direction of each unit sheet 10 is coincident with the direction of arrangement of the multiple electrodes 30.

Similarly, as described above, each stretchable line 20 extends in the X-direction. Thus, the direction of extension of each stretchable line 20 is also coincident with the direction of arrangement of the multiple electrodes 30.

The multiple unit sheets 10 described herein are connected to each other via junction sheets 40 (see FIGS. 5(*a*) and 6(*a*)), for example.

In the case of the present embodiment, the electrode sheet 100 includes, as the junction sheets 40, a first junction sheet 40*a* connecting the first unit sheet 10*a* and the second unit sheet 10*b* to each other and a second junction sheet 40*b* connecting the second unit sheet 10*b* and the third unit sheet 10*c* to each other, for example.

The outer shapes of the first junction sheet 40*a* and the second junction sheet 40*b* are the same shape with the same dimensions as viewed in plane, for example.

Each of the first junction sheet 40*a* and the second junction sheet 40*b* is formed in a substantially rectangular shape elongated in the Y-direction as viewed in plane, for example.

More specifically, in the case of the present embodiment, the first junction sheet 40*a* is arranged, for example, over a portion from the left edge of the first unit sheet 10*a* to the right edge of the second unit sheet 10*b*.

Similarly, the second junction sheet 40*b* is arranged, for example, over a portion from the left edge of the second unit sheet 10*b* to the right edge of the third unit sheet 10*c*.

Each of the junction sheets 40 (first junction sheet 40*a* and second junction sheet 40*b*) has a stretchable junction base 41 and multiple stretchable junction lines 43 formed on the stretchable junction base 41 and extending parallel with each other.

As shown in FIGS. 5(*a*) to 7, the stretchable lines 20 of one unit sheet 10 and the stretchable lines 20 of another unit sheet 10 are connected to each other via the stretchable junction lines 43. Accordingly, the junction sheet 40 connects adjacent ones of the unit sheets 10 to each other. Note that in the present invention, the junction sheet 40 may include a not-shown bonding layer and may connect adjacent ones of the unit sheets 10 to each other with the bonding layer.

More specifically, each of the junction sheets 40 (first junction sheet 40*a* and second junction sheet 40*b*) includes, as the multiple stretchable junction lines 43, multiple first stretchable junction lines 43*a* and multiple second stretchable junction lines 43*b*, for example.

Each of the multiple stretchable junction lines 43 (first stretchable junction lines 43*a* and second stretchable junction lines 43*b*) is directly formed on the lower surface (the lower surface in FIG. 7) of the stretchable junction base 41, for example.

Each of the multiple first stretchable junction lines 43*a* connects the first stretchable line 20*a* of one unit sheet 10 and the first stretchable line 20*a* of another unit sheet 10 to each other. Moreover, each of the multiple second stretchable junction lines 43*b* connects the second stretchable line 20*b* of one unit sheet 10 and the second stretchable line 20*b* of another unit sheet 10 to each other.

Each of the multiple first stretchable junction lines 43*a* extends in the X-direction. Moreover, the multiple first stretchable junction lines 43*a* are arranged in the Y-direction.

Similarly, each of the multiple second stretchable junction lines 43*b* extends in the X-direction. Moreover, the multiple second stretchable junction lines 43*b* are arranged in the Y-direction.

The width of each of the stretchable junction lines 43 (first stretchable junction lines 43*a* and second stretchable junction lines 43*b*) is, for example, substantially constant regardless of a position in the direction of extension thereof, and is set substantially equal to the width of the stretchable line 20. Note that as in Modification 1 described later, the width of the stretchable junction line 43 may be greater than the width of the stretchable line 20.

Note that in the case of the present embodiment, a sectional view (section along the C-C line shown in FIG. 1) of the second junction sheet 40*b* and the peripheral structure thereof is similar to a sectional view (FIG. 7) of the first junction sheet 40*a* and the peripheral structure thereof, and therefore, is not shown in the figure.

Each of the junction sheets 40 (first junction sheet 40*a* and second junction sheet 40*b*) further includes a stretchable junction cover 46 arranged, for example, on the lower surface side (the lower surface side in FIG. 7) of the stretchable junction base 41.

The stretchable junction cover 46 of the first junction sheet 40*a* is arranged, for example, over a portion between the stretchable cover 50 of the first unit sheet 10*a* and the stretchable cover 50 of the second unit sheet 10*b*.

Similarly, the stretchable junction cover 46 of the second junction sheet 40*b* is arranged, for example, over a portion between the stretchable cover 50 of the second unit sheet 10*b* and the stretchable cover 50 of the third unit sheet 10*c*.

The stretchable junction cover 46 is formed with openings 48 (see FIGS. 5(*a*) to 7), and the stretchable junction line 43 is interconnected with the corresponding stretchable line 20 via the opening 48.

More specifically, the openings 48 include, for example, a pair of right and left first openings 48*a* and a pair of right and left second openings 48*b*.

Of the pair of right and left first openings 48*a*, the right first opening 48*a* collectively includes, for example, part of right end portions of the first stretchable junction lines 43*a* and part of the corresponding first stretchable lines 20*a* as viewed in plane. The left first opening 48*a* collectively includes, for example, part of left end portions of the first stretchable junction lines 43*a* and part of the corresponding first stretchable lines 20*a* as viewed in plane.

Of the pair of right and left second openings 48*b*, the right second opening 48*b* collectively includes, for example, part of right end portions of the second stretchable junction lines 43*b* and part of the corresponding second stretchable lines 20*b* as viewed in plane. Similarly, the left second opening 48*b* collectively includes, for example, part of left end portions of the second stretchable junction lines 43*b* and part of the corresponding second stretchable lines 20*b* as viewed in plane.

The pair of right and left first openings 48*a* and the pair of right and left second openings 48*b* are set to have the same shape and dimensions. Each of the pair of right and left first openings 48*a* and the pair of right and left second openings 48*b* is formed elongated in the Y-direction.

In the first junction sheet 40*a*, one end portion of each of the first stretchable junction lines 43*a* is electrically and mechanically connected to the first connection terminal portion 25*a* of the corresponding first stretchable line 20*a* via the right first opening 48*a*. The other end portion of each of the first stretchable junction lines 43*a* is electrically and mechanically connected to the second connection terminal portion 25*b* of the corresponding first stretchable line 20*a* via the left first opening 48*a*.

More specifically, the first junction sheet 40*a* has the same number of first stretchable junction lines 43*a* as the number of first connection terminal portions 25*a* and the number of second connection terminal portions 25*b* of the first stretchable lines 20*a*, and the first connection terminal portion 25*a* and the second connection terminal portion 25*b* corresponding thereto are connected to each other via one first stretchable junction line 43*a*.

Similarly, in the first junction sheet 40*a*, one end portion of each of the second stretchable junction lines 43*b* is electrically and mechanically connected to the first connection terminal portion 25*a* of the corresponding second stretchable line 20*b* via the right second opening 48*b*. The other end portion of each of the second stretchable junction lines 43*b* is electrically and mechanically connected to the second connection terminal portion 25*b* of the corresponding second stretchable line 20*b* via the left second opening 48*b*.

More specifically, the first junction sheet 40*a* has the same number of second stretchable junction lines 43*b* as the number of first connection terminal portions 25*a* and the number of second connection terminal portions 25*b* of the second stretchable lines 20*b*, and the first connection terminal portion 25*a* and the second connection terminal portion 25*b* corresponding thereto are connected to each other via one second stretchable junction line 43*b*.

As described above, in the first junction sheet 40*a*, each stretchable junction line 43 electrically and mechanically connects the first connection terminal portion 25*a* of the first unit sheet 10*a* and the second connection terminal portion 25*b* of the second unit sheet 10*b* to each other.

In the second junction sheet 40*b*, one end portion of each of the first stretchable junction lines 43*a* is electrically and mechanically connected to the third connection terminal portion 25*c* of the corresponding first stretchable line 20*a* via the right first opening 48*a*. The other end portion of each of the first stretchable junction lines 43*a* is electrically and mechanically connected to the fourth connection terminal portion 25*d* of the corresponding first stretchable line 20*a* via the left first opening 48*a*.

More specifically, the second junction sheet 40*b* has the same number of first stretchable junction lines 43*a* as the number of third connection terminal portions 25*c* and the number of fourth connection terminal portions 25*d* of the first stretchable lines 20*a*, and the third connection terminal portion 25*c* and the fourth connection terminal portion 25*d* corresponding thereto are connected to each other via one first stretchable junction line 43*a*.

Similarly, in the second junction sheet 40*b*, one end portion of each of the second stretchable junction lines 43*b* is electrically and mechanically connected to the third connection terminal portion 25*c* of the corresponding second stretchable line 20*b* via the right second opening 48*b*. The other end portion of each of the second stretchable junction lines 43*b* is electrically and mechanically connected to the fourth connection terminal portion 25*d* of the corresponding second stretchable line 20*b* via the left second opening 48*b*.

More specifically, the second junction sheet 40*b* has the same number of second stretchable junction lines 43*b* as the number of third connection terminal portions 25*c* and the number of fourth connection terminal portions 25*d* of the second stretchable lines 20*b*, and the third connection terminal portion 25*c* and the fourth connection terminal portion 25*d* corresponding thereto are connected to each other via one second stretchable junction line 43*b*.

As described above, in the second junction sheet 40*b*, each stretchable junction line 43 electrically and mechanically connects the third connection terminal portion 25*c* of the second unit sheet 10*b* and the fourth connection terminal portion 25*d* of the third unit sheet 10*c* to each other.

As shown in FIGS. 1 and 4, a cutout-shaped portion 32 is formed at a lower left end portion of each electrode 30, and the lower left edge of the electrode 30 is, for example, in a shape upwardly inclined from the right side to the left side. In the unit sheet 10, the left end portion of each of the stretchable lines 20 which do not end at the electrodes 30 is upwardly inclined from the right side to the left side along the lower left edge of the electrode 30 arranged close to such a left end portion, for example. Moreover, a line-to-line distance between the left end portions of adjacent ones of the stretchable lines 20 gradually increases from the right side to the left side.

According to this configuration, a line-to-line distance between the stretchable junction lines 43 can be sufficiently ensured at the left edge of the unit sheet 10. Thus, when the stretchable junction lines 43 and the stretchable lines 20 are electrically connected to each other with the junction sheet 40 and the corresponding unit sheet 10 positioned relative to each other, even if the stretchable junction lines 43 and the corresponding unit sheet 10 are slightly shifted from each other in the Y-direction (direction of the width of the stretchable junction line 43), the stretchable junction lines 43 are more easily connected to the corresponding stretchable lines 20 by properly positioning the stretchable junction lines 43 relative to the corresponding stretchable lines 20.

Each of the stretchable junction base 41 and the stretchable junction cover 46 contains, for example, thermoplastic resin as do the stretchable base 11 and the stretchable cover 50.

Materials forming the stretchable junction base 41 and the stretchable junction cover 46 are, but not specifically limited to, an elastomer material similar to those of the stretchable base 11 and the stretchable cover 50, for example.

Note that each of the stretchable junction base 41 and the stretchable junction cover 46 is sufficient when made of at least a material having insulating properties and stretchability and may be made of a material different from those of the stretchable base 11 and the stretchable cover 50.

For example, the thickness dimension of the stretchable junction base 41 is, but not specifically limited to, preferably 100 μm or less and more preferably 25 μm or less, for sufficiently ensuring the stretchability of the electrode sheet 100.

For example, the thickness dimension of the stretchable junction cover 46 is, but not specifically limited to, preferably 100 μm or less and more preferably 25 μm or less, for sufficiently ensuring the stretchability of the electrode sheet 100.

In the case of the present embodiment, each of the electrode 30, the stretchable line 20, and the stretchable junction line 43 is, for example, a coating film including a conductive filler and a binder containing thermoplastic resin.

Thus, upon manufacturing of the electrode sheet 100, each of the stretchable lines 20 and the stretchable junction lines 43 is heated and pressurized, and accordingly, the stretchable junction line 43 and the connection terminal portion 25 corresponding thereto are fused to each other via the opening 48.

That is, the stretchable line 20 and the stretchable junction line 43 can be electrically and mechanically connected to each other with a simpler structure without a conductive adhesive, an anisotropic conductive film (ACF), or an anisotropic conductive paste (ACP), and therefore, the manufacturability of the electrode sheet 100 can be improved. Since the stretchable line 20 and the stretchable junction line 43 are fused to each other, a state in which the junction sheet 40 and the unit sheet 10 corresponding thereto are connected to each other can be favorably maintained.

In addition, since each of the electrode 30, the stretchable line 20, and the stretchable junction line 43 includes a binder containing the thermoplastic resin, these components can favorably adjust to stretching and contraction of the stretchable base 11.

The conductive filler includes, for example, silver, gold, platinum, carbon, copper, aluminum, cobalt, nickel, or an alloy thereof.

The thermoplastic resin may include, for example, thermoplastic elastomer materials such as urethane resin, acrylic resin, and silicone rubber. As the thermoplastic resin, thermoplastic resin with a low Young's modulus is preferably selected such that the elastic modulus of each of the electrode 30, the stretchable line 20, and the stretchable junction line 43 in a coated state is equal to or less than the elastic modulus of the stretchable base 11. One type of elastomer material may be used, or multiple types of elastomer materials may be used in combination.

A method for forming each of the electrode 30, the stretchable line 20, and the stretchable junction line 43 is not specifically limited, and for example, these portions may be formed by a printing method. Examples of the printing method may include, but not specifically limited to, a screen printing method, an ink-jet printing method, a gravure printing method, and an offset printing method.

The thickness of each of the electrode 30 and the stretchable line 20 is, but not specifically limited to, preferably 10 μm or more and more preferably about 20 μm.

Similarly, the thickness of the stretchable junction line 43 is, but not specifically limited to, preferably 10 μm or more and more preferably about 20 μm.

Further, each unit sheet 10 has, for example, a bonding layer 61 for bonding the electrode sheet 100 to the attachment target (e.g., sheet 400 described later). Note that each unit sheet 10 may have an adhesive layer (not shown) instead of the bonding layer 61.

Each unit sheet 10 includes a first release film 71 and a second release film 76. The first release film 71 is stacked on the upper surface side of the bonding layer 61 so as to be easily detachable from the bonding layer 61. Similarly, the second release film 76 is stacked on the lower surface side of the stretchable base 11 so as to be easily detachable from the stretchable base 11.

The bonding layer 61 is formed, for example, by coating of a bonding material. More specifically, the bonding layer 61 is, for example, a single film formed in such a manner that the bonding material is applied to a desired thickness on the upper surface of the first release film 71 and is subsequently cured by thermal processing. Thus, as compared to a case where the bonding layer 61 includes a core such as nonwoven fabric or paper, the bonding layer 61 can favorably adjust to stretching and contraction of the stretchable base 11. Note that at a stage before the bonding layer 61 is stacked on the stretchable cover 50 upon manufacturing of the electrode sheet 100, the bonding layer 61 also has a release film (not shown) on the surface on the side opposite to the first release film 71. The bonding layer 61 can be bonded to the stretchable cover 50 as a result of detaching the release film from the bonding layer 61.

Examples of the bonding material to be used may include, but not specifically limited to, acrylic-based resin.

Upon use of the electrode sheet 100, the first release film 71 is first detached from the bonding layer 61 such that the bonding layer 61 is exposed, for example. Then, the electrode sheet 100 can be bonded to the attachment target via the bonding layer 61. Next, the second release film 76 is detached from the stretchable base 11 such that the stretchable base 11 is exposed on the upper surface side of the electrode sheet 100.

In this manner, the electrode sheet 100 is bonded to the attachment target before detachment of the second release film 76 so that the electrode sheet 100 can be bonded to an intended area while twist of the electrode sheet 100 is reduced.

The material of each of the first release film 71 and the second release film 76 includes, but not specifically limited to, polyethylene terephthalate (PET) and paper, for example. The first release film 71 and the second release film 76 may be made of the same material, or may be made of different materials.

As shown in FIGS. 1 and 4, in the case of the present embodiment, the unit sheet 10 has multiple through-holes 16 arranged at positions each corresponding to the electrodes 30.

In the case of the present embodiment, the through-holes 16 are arranged at the positions corresponding to the electrodes 30 in one-to-one correspondence.

Each through-hole 16 is formed, for example, so as to penetrate the first release film 71, the bonding layer 61, and the stretchable cover 50 in the thickness direction of each layer. Thus, a portion of each electrode 30 corresponding to the through-hole 16 is exposed on the upper surface side of the electrode sheet 100.

Upon manufacturing of the electrode sheet 100, an inspection probe (not shown) contacts the electrode 30 through the through-hole 16 so that the properties of the electrode 30 and the stretchable line 20 corresponding thereto can be electrically inspected.

In the case of the present embodiment, an external connection terminal portion 80 is provided at the right end of the first unit sheet 10*a* as shown in FIG. 4. As shown in FIGS. 2 and 3, the external connection terminal portion 80 is interposed, for example, between the stretchable cover 50 and the stretchable base 11.

The external connection terminal portion 80 has, for example, the same number of external connection terminals 83 as the number of electrodes 30 included in the electrode sheet 100, and the external connection terminals 83 are connected to the electrodes 30 in one-to-one correspondence. Each electrode 30 is electrically connected to the electrode selector and the biological information acquirer via the corresponding external connection terminal 83.

More specifically, the electrode sheet 100 includes, as the external connection terminal portion 80, a first external connection terminal portion 80*a* connected to the first stretchable lines 20*a* and a second external connection terminal portion 80*b* connected to the second stretchable lines 20*b*, for example.

The external connection terminal portion 80 (first external connection terminal portion 80*a* and second external connection terminal portion 80*b*) has, for example, a non-stretchable base 81 and lead lines 82 formed on the non-stretchable base 81 and connected to the stretchable lines 20.

As shown in FIG. 4, the first external connection terminal portion 80*a* has, for example, the same number of lead lines 82 as the number of first stretchable lines 20*a* included in the electrode sheet 100, and the lead lines 82 are mechanically and electrically connected to the first stretchable lines 20*a* in one-to-one correspondence. Similarly, the second external connection terminal portion 80*b* has, for example, the same number of lead lines 82 as the number of second stretchable lines 20*b* included in the electrode sheet 100, and the lead lines 82 are mechanically and electrically connected to the second stretchable lines 20*b* in one-to-one correspondence.

Each lead line 82 is formed, for example, on the lower surface of the non-stretchable base 81. Each lead line 82 extends, for example, in the X-direction.

In the case of the present embodiment, for example, part of the lead line 82 forms the external connection terminal 83.

More specifically, a left end portion of each lead line 82 is connected to the right end portion of the corresponding stretchable line 20, and a right end portion of each lead line 82 forms the external connection terminal 83.

The external connection terminals 83 are individually connected, for example, to multiple switches 96*a* included in a later-described switcher 96.

The non-stretchable base 81 may be formed of a resin film, for example. A resin material forming the resin film includes, but not specifically limited to, polyethylene, polystyrene, polypropylene, or polyester, for example.

The thickness of the non-stretchable base 81 is, for example, preferably 100 μm or less and more preferably 50 μm or less.

As in the stretchable line 20, the lead line 82 is a coating film including a conductive filler and a binder containing thermoplastic resin, for example. Thus, upon manufacturing of the electrode sheet 100, each of the lead lines 82 and the stretchable lines 20 is heated and pressurized, and accordingly, the lead line 82 and the stretchable line 20 corresponding thereto are fused to each other.

The thickness of the lead line 82 is, but not specifically limited to, preferably 10 μm or more and more preferably about 20 μm.

As described above, in the case of the present embodiment, the external connection terminal portion 80 is provided at the end of one of the multiple unit sheets 10 positioned at one end in the direction of arrangement of the multiple unit sheets 10, the end being positioned on the side opposite to the other unit sheets 10, as shown in FIG. 4. The external connection terminal portion 80 has the non-stretchable base 81 and the lead lines 82 formed on the non-stretchable base 81 and connected to the stretchable lines 20, and part of each lead line 82 forms the external connection terminal 83.

In the case of the present embodiment, the biological information acquisition system 200 (electrode sheet 100, electrode selector, and biological information acquirer) is used for acquiring an electrocardiogram waveform of the biological body 300.

The electrocardiogram waveform is acquired using the biological information acquisition system 200 in a state in which a subject lies on the attachment target (e.g., the sheet 400 shown in FIG. 12) to which the multiple electrode sheets 100 are attached, for example. Thus, for each electrode 30, the relevant electrode 30, the clothes of the subject and the sheet 400 (insulator 350), and the skin 360 of the subject (biological body 300) form the capacitor 370. Note that in the case of the present embodiment, the stretchable base 11 and the stretchable cover 50 are made of the materials having the insulating properties as described above, and therefore, these layers also form the insulator 350 together with the sheet 400.

Hereinafter, the multiple electrode sheets 100 bonded to one attachment target will be sometimes collectively referred to as an electrode sheet unit 150.

Figure 11:
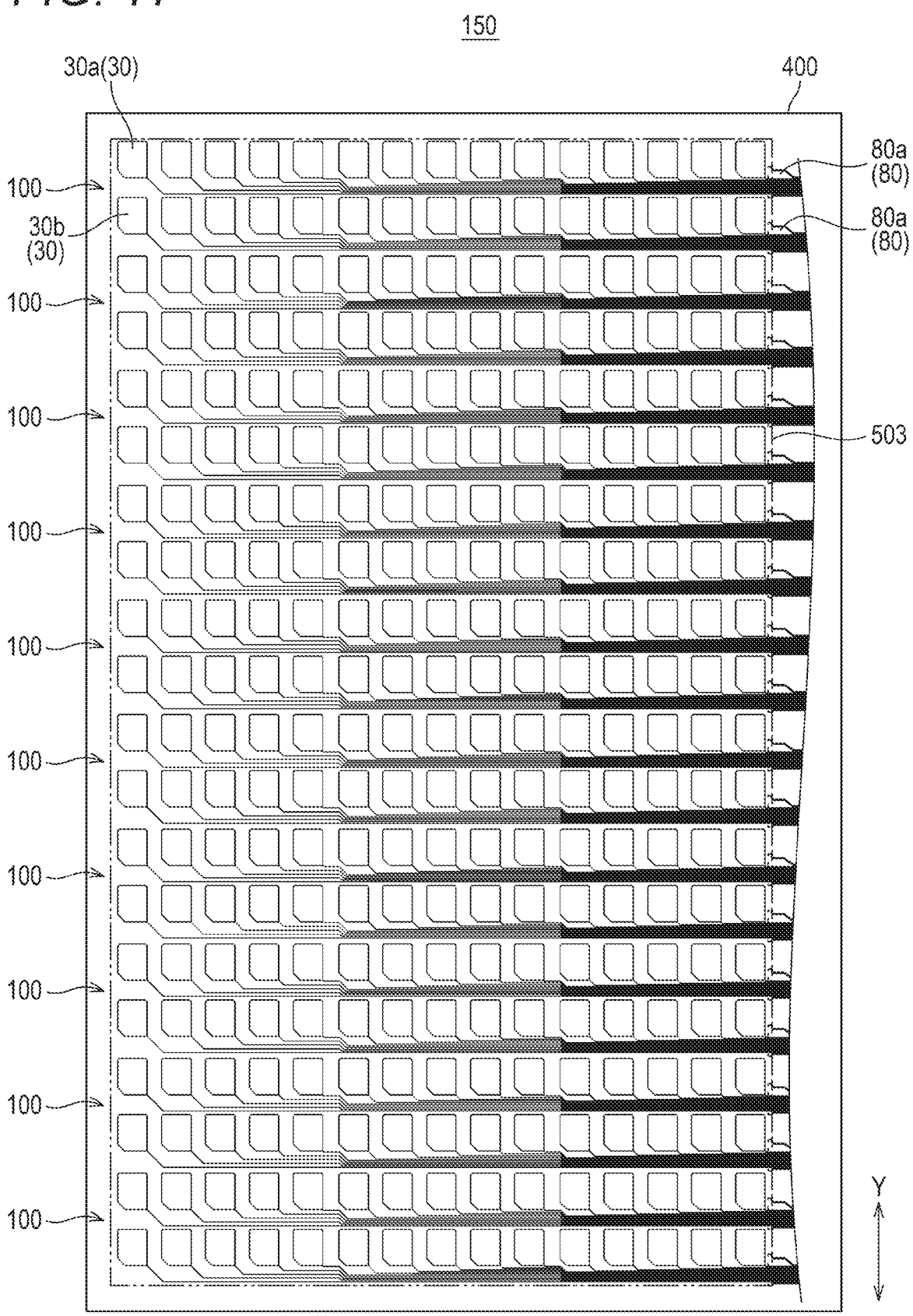
FIG. 11 is a plan view of an electrode sheet unit in the first embodiment.
Figure 12:
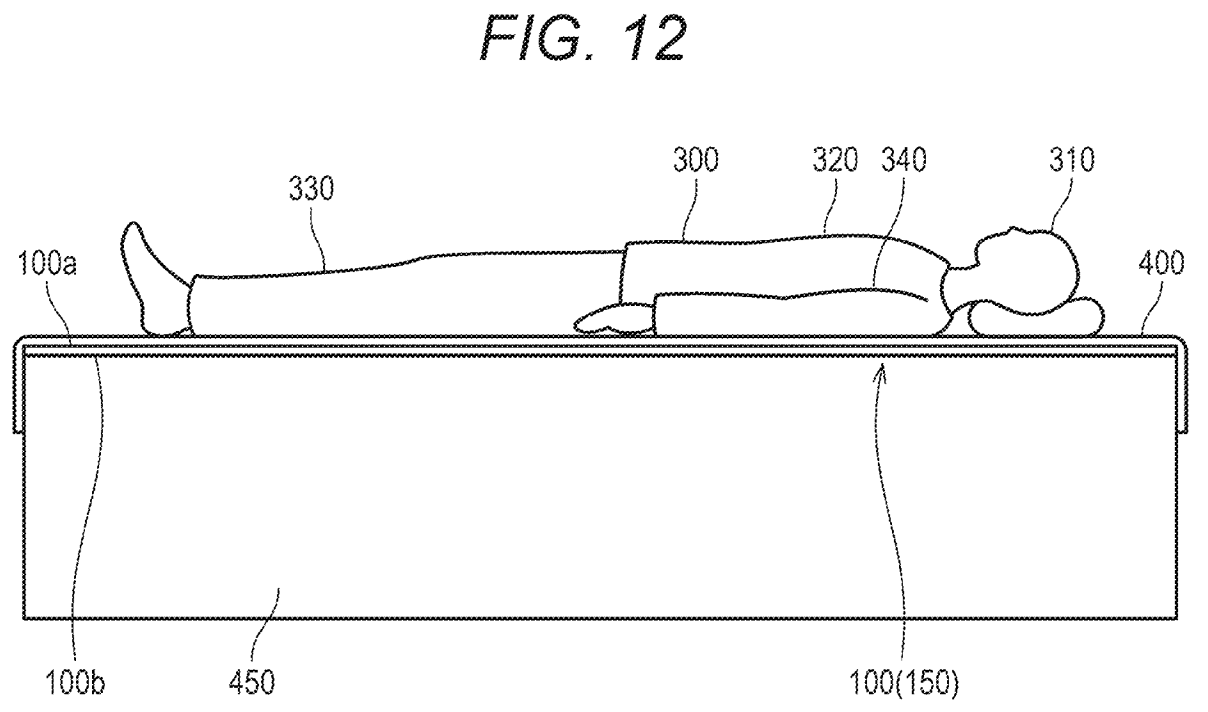

As shown in FIGS. 11 and 12, the sheet 400 to which the electrode sheet unit 150 is bonded is placed over a bed 450, for example. Note that FIG. 11 shows the surface (front surface) of the sheet 400 on the side contacting the skin of the subject. Moreover, in FIGS. 11, 14(*a*), 14(*b*), and 14(*c*), the multiple electrodes 30 of the components of the electrode sheet unit 150 are selectively indicated by solid lines.

In the electrode sheet unit 150, the multiple electrodes 30 included in each electrode sheet 100 are arranged in an array. More specifically, in the electrode sheet unit 150, the electrode sheets 100 are arranged in the Y-direction such that the multiple electrodes 30 are arrayed in a square grid pattern as viewed in plane. In the electrode sheet unit 150, the multiple electrodes 30 are separated from each other and arranged at equal intervals in the X-direction, and are also separated from each other and arranged at equal intervals in the Y-direction.

Figure 13:
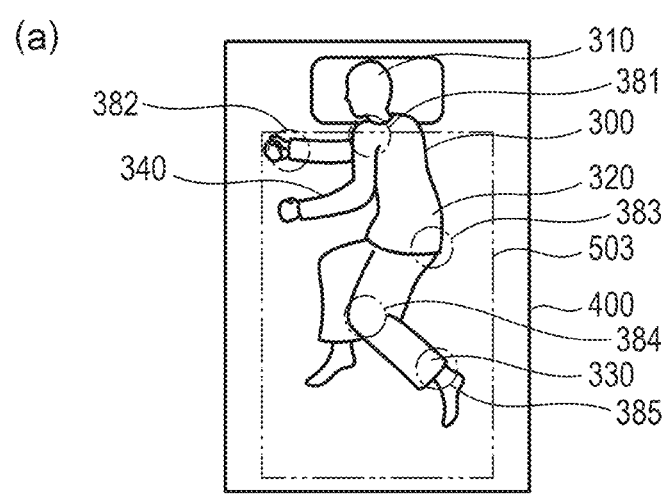
FIGS. 13(a), 13(b), and 13(c) are schematic views showing the posture of a biological body in the first embodiment, FIG. 13(a) showing a left lateral decubitus position, FIG. 13(b) showing a supine position, and FIG. 13(c) showing a right lateral decubitus position.
Figure 13:
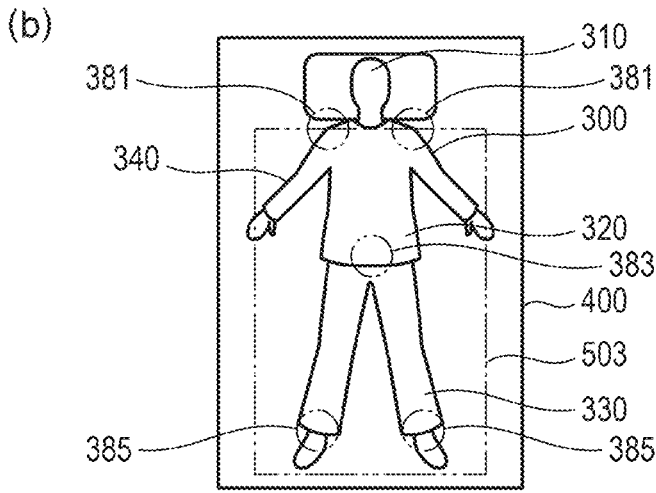
Figure 13:
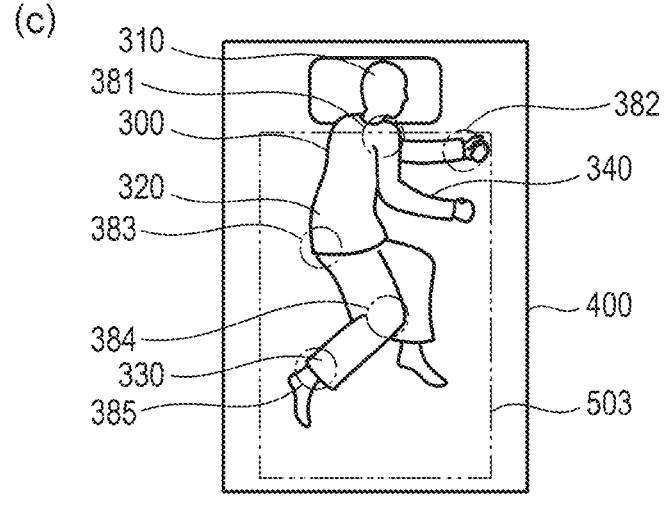

The electrode sheet unit 150 is configured, for example, such that at least the entirety of the trunk 320 of the biological body 300 is within an arrangement region 503 (region indicated by a chain double-dashed line in FIGS. 11 and 13(*a*) to 13(*c*)) where the multiple electrodes 30 are arranged in the electrode sheet unit 150, as viewed in plane. Note that FIGS. 13(*a*) to 13(*c*) shows an example where the trunk 320, legs 330, and arms 340 are mainly arranged in the arrangement region 503 for the electrodes 30, but the present invention is not limited to this example and the electrode sheet unit 150 may be configured such that the entirety of the biological body 300 including the head 310 is within the arrangement region 503.

In the example shown in FIG. 11, 10 electrode sheets 100 are arranged in the Y-direction. In the electrode sheet unit 150, the multiple electrodes 30 are arranged, for example, in 20 rows in the Y-direction, and each row includes 15 electrodes 30 arranged in the X-direction. Thus, the electrode sheet unit 150 includes 300 electrodes 30 in 20 rows and 15 columns.

In the arrangement region 503 for the multiple electrodes 30, the biological body 300 lies in such a posture that the head 310 of the biological body 300 is arranged on one side (upper side in FIG. 11) in the Y-direction and the legs 330 of the biological body 300 are arranged on the other side (lower side in FIG. 11) in the Y-direction, for example.

Note that in the present invention, the number of electrode sheets 100 included in the electrode sheet unit 150 and arrangement thereof are not limited to those of this example and are settable as necessary according to, e.g., the use of the biological information acquisition system 200 or the outer diameter dimension of the attachment target.

The electrode sheet unit 150 includes the multiple electrode sheets 100. Thus, even if some of the electrodes 30 or the stretchable lines 20 have lost their functions due to, e.g., break during long-term use of the electrode sheet unit 150, it is enough to replace the electrode sheet 100 having the relevant electrodes 30 or stretchable lines 20 with another new electrode sheet 100. That is, the electrode sheet unit 150 can be easily repaired.

Figure 10:
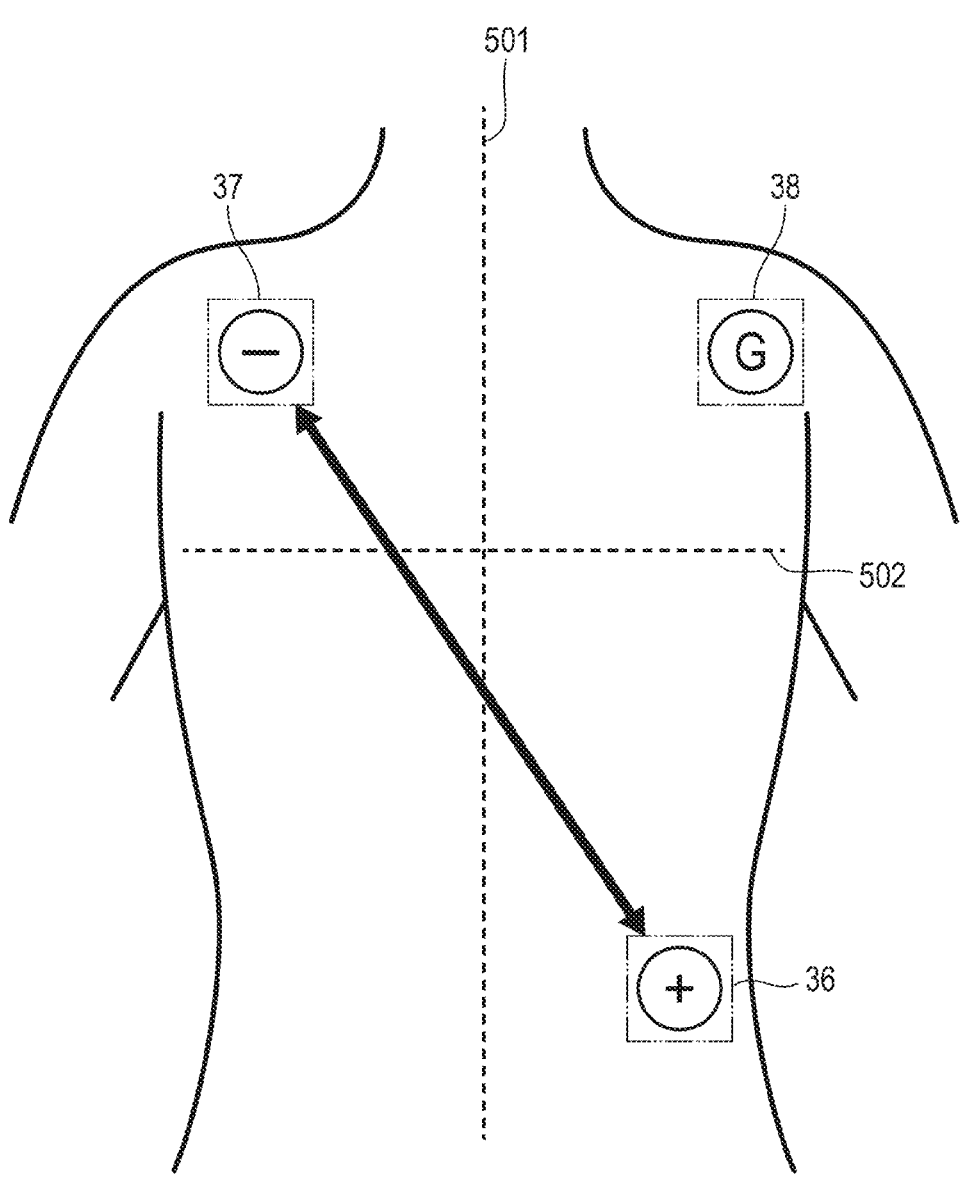
FIG. 10 is a view for describing a three-point induction method in the first embodiment.

In the case of the present embodiment, the electrode selector selects the electrodes 30 at three positions suitable for acquisition of an electrocardiogram waveform by a three-point induction method shown in FIG. 10, and the biological information acquirer acquires the electrocardiogram waveform as the biological information by the three-point induction method, for example.

Note that generally in the case of acquiring an electrocardiogram waveform by the three-point induction method, monitor induction includes II induction, MCL1 induction, MCL5 induction, NASA induction, and II induction is employed as one example in the present embodiment.

Hereinafter, in the upper body of the biological body 300 shown in FIG. 10, with reference to a virtual line 501, the right portion will be referred to as the left side of the body, and the left portion will be referred to as the right side of the body. Also, in the upper body of the biological body 300 shown in FIG. 10, with reference to a virtual line 502, the upper portion will be referred to as the upper portion of the upper body, and the lower portion will be referred to as the lower portion of the upper body.

As one example, the electrode selector selects, as a positive electrode 36, the electrode 30 having the maximum electrostatic capacitance from the electrodes 30 arranged at positions corresponding to the lower portion of the upper body (or a portion below the lower portion of the upper body) of the biological body 300 and the left side of the biological body 300. Similarly, the electrode selector selects, as a negative electrode 37, the electrode 30 having the maximum electrostatic capacitance from the electrodes 30 arranged at positions corresponding to the upper portion of the upper body of the biological body 300 and the right side of the biological body 300, as one example. The electrode selector selects, as a ground electrode 38, the electrode 30 having the maximum electrostatic capacitance from the electrodes 30 arranged at positions corresponding to the upper portion of the upper body of the biological body 300 and the left side of the biological body 300. Then, the biological information acquirer performs induction equivalent to II induction with these electrodes 30 (positive electrode 36, negative electrode 37, and ground electrode 38) at three positions, thereby acquiring an electrocardiogram waveform.

Note that the "positions corresponding to the biological body 300" as described herein are, for example, positions corresponding to (overlapping with) the biological body 300 as viewed in plane (when viewed in the direction perpendicular to the plane of the electrode sheet 100).

Moreover, in the present invention, the positions of the electrodes 30 at three positions selected by the electrode selector are not limited to this example and are changeable and settable as necessary.

Further, in the present invention, the type of monitor induction when an electrocardiogram waveform is acquired using the biological information acquisition system 200 is not limited to II induction.

More specifically, in the case of the present embodiment, the multiple electrodes 30 are individually arranged at the positions corresponding to the parts of the biological body 300 as described above, and therefore, the electrodes 30 at three positions to be selected are changed as necessary so that induction equivalent to, e.g., MCL1 induction, MCL5 induction, or NASA induction can be performed.

Since the electrode sheet 100 is flexible as described above, ones, which are arranged at the positions corresponding to the biological body 300, of the multiple electrodes 30 included in the electrode sheet 100 can be arranged in accordance with the uneven body surface of the biological body 300.

Thus, it can be expected that each of the electrodes 30 at three positions selected by the electrode selector is favorably arranged along the uneven surface of the biological body 300 and the capacitance of the capacitor 370 formed by the electrode 30, the insulator 350, and the biological body 300 is equal among the electrodes 30 at three positions. Thus, a more-accurate electrocardiogram waveform can be acquired.

Figure 15:
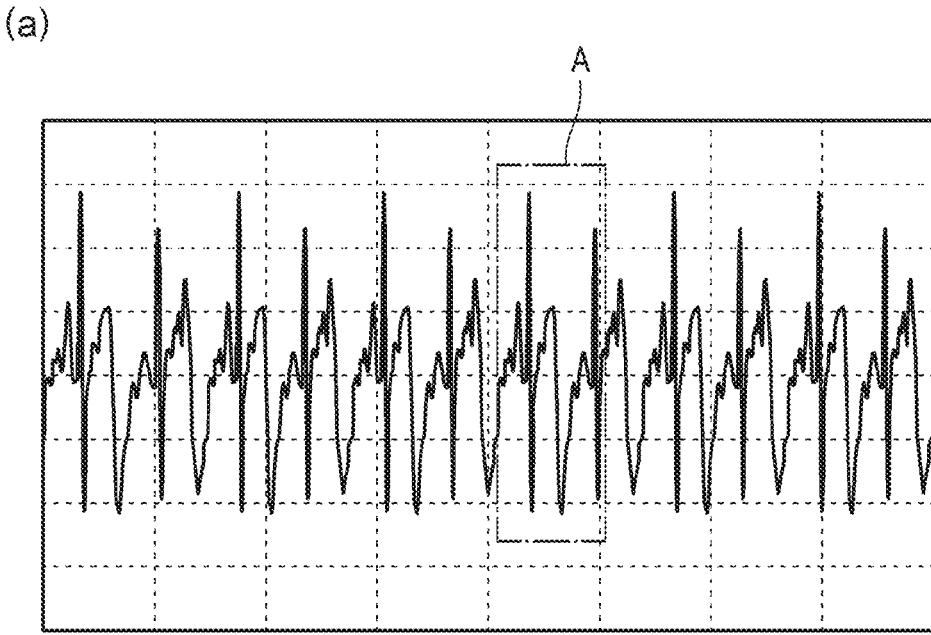
FIG. 15(a) is an electrocardiogram acquired using the biological information acquisition system according to the first embodiment.
FIG. 15(b) is a partially-enlarged view of a portion A shown in FIG. 15(a)
Figure 15:
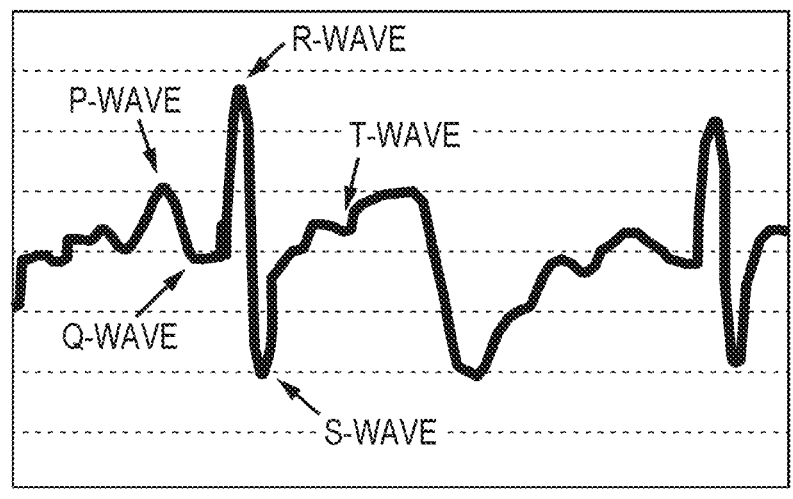

FIGS. 15(*a*) and 15(*b*) are electrocardiograms acquired using the biological information acquisition system 200 of the present embodiment by the three-point induction method (II induction). As shown in FIGS. 15(*a*) and 15(*b*), the waveforms of a P-wave, an R-wave, a Q-wave, an S-wave, and a T-wave which are the characteristics of the electrocardiogram waveform are observable.

The electrode selector detects, as an electric parameter, a change in the electrostatic capacitance, for example. Then, the electrode selector determines the posture of the biological body 300 based on the detected change in the electrostatic capacitance, and selects the electrodes 30 to be used for acquisition of the biological information based on a posture determination result.

With this configuration, in a state in which the electrode sheets 100 are arranged along the biological body 300, even if the position of each part of the biological body 300 relative to the multiple electrodes 30 has changed due to a change in the posture of the biological body 300, the electrodes 30 to be used for acquisition of the biological information can be properly selected. Thus, the biological information can be efficiently and more accurately acquired regardless of the posture of the biological body 300.

In the case of the present embodiment, the electrodes 30 at three positions suitable for acquisition of an electrocardiogram waveform by the three-point induction method can be properly selected based on the posture determination result.

Figure 9:
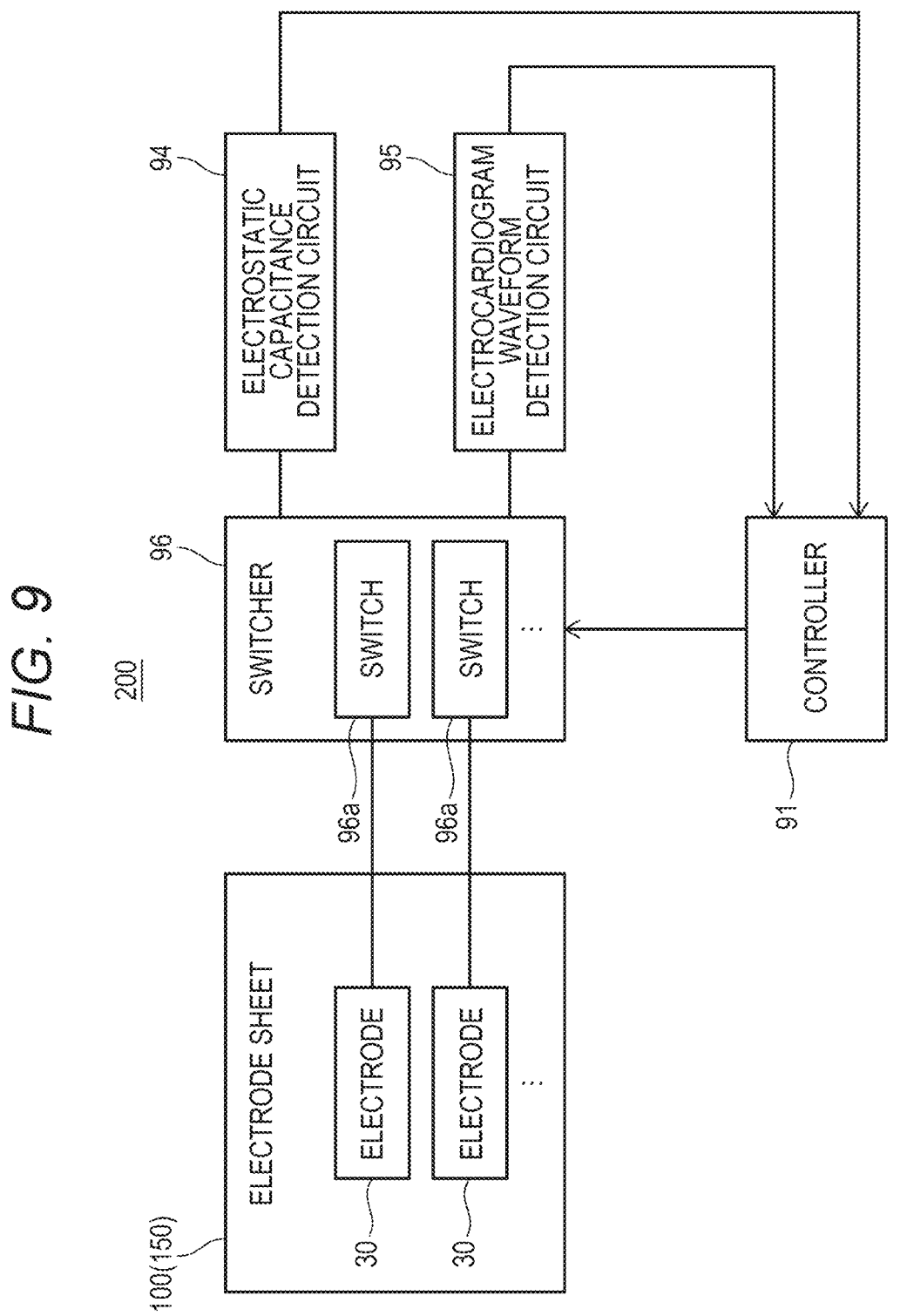
FIG. 9 is a block diagram of a biological information acquisition system according to the first embodiment.

More specifically, as shown in FIG. 9, the biological information acquisition system 200 includes, for example, an electrostatic capacitance detection circuit 94 that detects data necessary for calculation of the electrostatic capacitance accumulated in each electrode 30 and an electrocardiogram waveform detection circuit 95 that detects data necessary for acquisition of the electrocardiogram waveform.

Further, the biological information acquisition system 200 includes the switcher 96 connected to the external connection terminal portion 80 of the electrode sheet 100, and a controller 91 that controls operation of the switcher 96.

In the case of the present embodiment, the controller 91, the electrostatic capacitance detection circuit 94, and the switcher 96 together function as the electrode selector as one example. Similarly, as one example, the controller 91 and the electrocardiogram waveform detection circuit 95 together function as the biological information acquirer.

The data detected by the electrostatic capacitance detection circuit 94 and the data detected by the electrocardiogram waveform detection circuit 95 are input to the controller 91, for example. The controller 91 calculates the electrostatic capacitance of each electrode 30 based on the data detected by the electrostatic capacitance detection circuit 94. Moreover, the controller 91 generates electrocardiogram waveform data based on the data detected by the electrocardiogram waveform detection circuit 95.

The controller 91 includes a read only memory (ROM) that stores and holds a control program (program), a central processing unit (CPU) that executes control operation according to the control program, and a random access memory (RAM) functioning as, e.g., a work area of the CPU.

As the controller 91, a terminal such as a tablet PC configured such that a controller and a display (not shown) are integrated can be used, for example.

The controller 91 performs, by control of operation of the switcher 96, an operation of individually connecting the electrodes 30 to the electrostatic capacitance detection circuit 94 and an operation of connecting the electrodes 30 at three positions suitable for acquisition of an electrocardiogram waveform to the electrocardiogram waveform detection circuit 95. That is, the controller 91 switches, by control of operation of the switcher 96, a mode between a mode for measuring the electrostatic capacitance and a mode for acquiring an electrocardiogram waveform.

As shown in FIG. 9, the switcher 96, for example, includes the number of switches % a corresponding to the number of electrodes 30 included in the electrode sheet 100. In the case of the present embodiment, the switcher 96 includes, as one example, four switches 96a (hereinafter, referred to as a first switch, a second switch, a third switch, and a fourth switch) for one electrode 30. Note that in FIG. 9, the first to fourth switches are not shown.

For example, the controller 91 turns on/off the first switch of the four switches 96a, thereby switching a state between a state (ON) in which the corresponding electrode 30 and the electrostatic capacitance detection circuit 94 are connected to each other and a state (OFF) in which the foregoing connection is blocked.

Moreover, the controller 91 individually turns on/off the remaining three switches 96a (second switch, third switch, and fourth switch), thereby switching a state between a state (ON) in which the corresponding electrode 30 and the electrocardiogram waveform detection circuit 95 are connected to each other and a state (OFF) in which the foregoing connection is blocked, for example. More specifically, the controller 91 turns on the second switch to select the corresponding electrode 30 as the positive electrode 36, turns on the third switch to select the corresponding electrode 30 as the negative electrode 37, and turns on the fourth switch to select the corresponding electrode 30 as the ground electrode 38.

Each electrode 30 is connected to the corresponding switch 96a via the corresponding stretchable line 20 and the corresponding external connection terminal 83.

The controller 91 (electrode selector) connects, by control of operation of the switcher 96, the electrodes 30 to the electrostatic capacitance detection circuit 94 one by one in order. The electrostatic capacitance detection circuit 94 applies a constant current to each electrode 30 for a certain time, thereby detecting a change in a voltage value. Then, based on the amount of detected voltage value change, the controller 91 calculates the electrostatic capacitance accumulated in the electrode 30. In the case of the present embodiment, the controller 91 individually calculates the electrostatic capacitance data for all the electrodes 30 included in the electrode sheet unit 150. The controller 91 integrates a group of electrostatic capacitance data calculated for the electrodes 30, and generates image data (see FIGS. 19(*a*) to 19(*c*) in Examples 1 to 3 described later) indicating, in grayscale, the distribution of the electrostatic capacitance in the arrangement region 503 for the electrodes 30. Note that the controller 91 may display the generated image data on the display (not shown), for example.

In the arrangement region 503 for the electrodes 30, as the electrode 30 is positioned closer to the biological body 300, the electrostatic capacitance calculated in the electrode 30 increases due to influence of the permittivity of the biological body 300. As a result, the image data as shown in FIGS. 19(a) to 19(c) is generated according to the posture of the biological body 300.

More specifically, on the generated image data, a portion positioned closer to the biological body 300 has a higher brightness (more whitened), and a portion positioned farther from the biological body 300 has a lower brightness (more blackened). Thus, on the image data indicating the distribution of the electrostatic capacitance, the posture of the biological body 300 can be measured as a silhouette.

In the case of the present embodiment, the electrode selector determines the posture of the biological body 300 from the generated image data by using artificial intelligence, for example.

More specifically, the artificial intelligence is, as one example, a neural network. Using a learned model having learnt the feature amount of an image (image data indicating the distribution of the electrostatic capacitance in the case of the present embodiment) targeted for inspection, the artificial intelligence determines the posture of the biological body 300 from the generated image data. In the case of the present embodiment, the artificial intelligence determines (categorizes), as one example, the posture of the biological body 300 as any of a left lateral decubitus position (see FIG. 13(a)), a supine position (see FIG. 13(b)), and a right lateral decubitus position (see FIG. 13(c)). Then, the controller 91 selects the electrodes 30 at three positions suitable for acquisition of an electrocardiogram waveform in the determined posture.

In the case of the present embodiment, the controller 91 has the artificial intelligence.

As described above, in the case of the present embodiment, the electrode selector selects, by determination using the artificial intelligence, the electrodes 30 to be used for acquisition of the biological information.

With this configuration, the electrodes 30 suitable for acquisition of desired biological information can be easily selected, and therefore, the biological information can be more efficiently acquired.

Moreover, as described above, the electrode sheet 100 includes the stretchable base 11 which is a thin sheet material stretchable in at least one direction of in-plane directions, and each of the electrodes 30, the stretchable lines 20, and the stretchable junction lines 43 can favorably adjust to stretching and contraction of the stretchable base 11. That is, the electrode sheet 100 is stretchable and curvable in accordance with the uneven body surface of the biological body 300.

With this configuration, each electrode 30 can favorably closely contact the corresponding part of the biological body 300, and therefore, the electrostatic capacitance of each electrode 30 can be more accurately measured. Thus, the posture of the biological body 300 can be more definitely determined.

In the case of the present embodiment, the sheet 400 to which the electrode sheet unit 150 is bonded is placed over the bed 450, as described above.

According to the biological information acquisition system 200 of the present embodiment, the electrode sheet 100 does not need to be fixed to the biological body 300. In addition, even when the posture of the biological body 300 has changed, the electrodes 30 to be used for acquisition of the electrocardiogram waveform can be selected as necessary. Thus, upon acquisition of the electrocardiogram waveform, the subject (biological body 300) does not need to lie in the same posture for a long period of time, and therefore, pressure ulcer (bedsore) can be reduced. That is, the less-invasive electrode sheet 100 and therefore the less-invasive biological information acquisition system 200 can be achieved with a comfortable feeling of use.

Moreover, in the case of the present embodiment, the electrode sheet 100 is flexible so that the flexibility of bedclothes (sheet 400 and bed 450) to which the electrode sheet 100 is bonded can be sufficiently maintained. Thus, when the biological body 300 lies on the bedclothes, the body pressure of the biological body 300 is moderately applied to the electrode sheet 100, and therefore, the electrode sheet 100 can be more favorably arranged in accordance with the uneven body surface of the biological body 300.

Further, e.g., in a state in which the subject is covered with a comforter and the posture of the subject is not viewable, the posture of the subject can be understood by the biological information acquisition system 200. Thus, in the fields of, for example, nursing care, the biological information acquisition system 200 detects how long a person requiring care is in the same posture so that an objective decision on, e.g., whether or not there is a risk of pressure ulcer (bedsore) can be made.

As shown in FIG. 12, the electrode sheet unit 150 is bonded, via the bonding layer 61, to the surface (back surface) of the sheet 400 on the side opposite to the surface contacting the skin of the subject, for example. Thus, each electrode sheet 100 is bonded to the attachment target in such a posture that the surface (one surface 100a) on which the bonding layer 61 is formed faces up and the opposite surface (other surface 100b) thereof faces down.

With this configuration, direct contact between the subject and the electrode sheet unit 150 on the sheet 400 can be reduced, and therefore, a state in which the electrode sheet unit 150 is bonded to the sheet 400 can be favorably maintained.

Note that the surface of the sheet 400 to which the electrode sheet unit 150 is bonded may be the front surface of the sheet 400.

As the sheet 400, a general sheet made of a material such as cotton, linen, polyester, silk, and wool is used, for example. The representative value of the elastic modulus (Young's modulus) of such a material is 2 GPa or more and 20 GPa or less. This material has a high flexibility, but has a low stretchability.

On the other hand, in the case of the present embodiment, the elastic modulus (Young's modulus) of the electrode sheet 100 is, for example, set at least to 500 MPa or less, preferably 50 MPa or less, and more preferably 30 MPa or less.

That is, in the case of the present embodiment, the elastic modulus (Young's modulus) of the electrode sheet 100 is set lower than the elastic modulus of the attachment target (sheet 400). With this configuration, excessive stretching of the electrode sheet 100 accompanied by stretching of the attachment target can be reduced. As a result, an increase in the resistance value of the stretchable line 20 can be suppressed, disconnection of the stretchable line 20 can be reduced, and a high durability of the electrode sheet 100 can be achieved.

Figure 14:
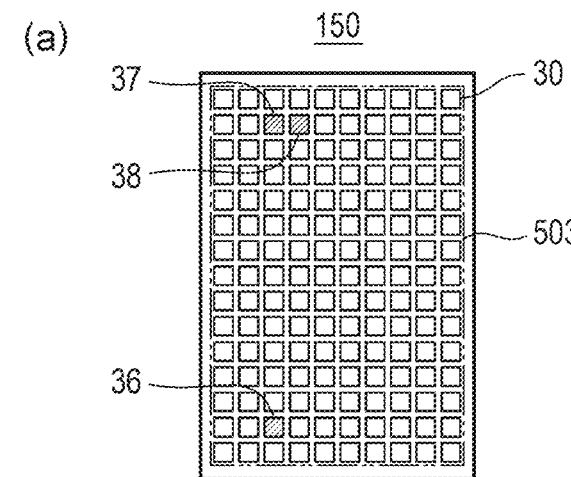
FIGS. 14(a), 14(b), and 14(c) are plan views showing one example of electrodes at three positions selected by an electrode selector in the first embodiment, FIG. 14(a) showing electrodes at three positions selected in the posture of FIG. 13(a), FIG. 14(b) showing electrodes at three positions selected in the posture of FIG. 13(b), and FIG. 14(c) showing electrodes at three positions selected in the posture of FIG. 13(c)
Figure 14:
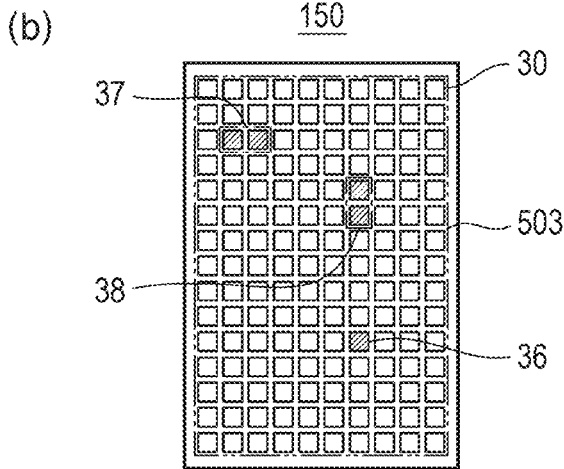
Figure 14:
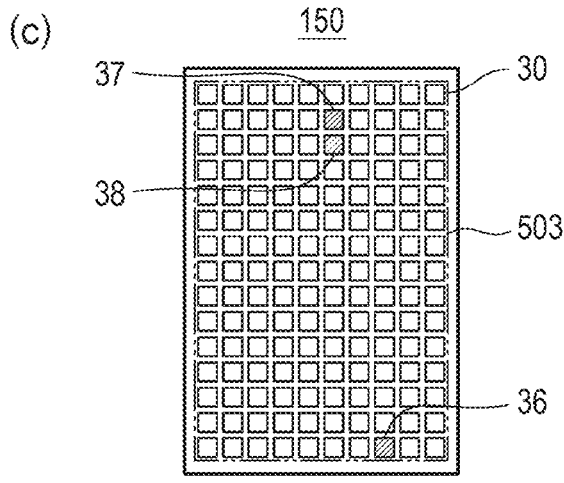

Hereinafter, one example of operation of the biological information acquisition system 200 will be described using FIGS. 13(a) to 14(c). Note that in description below, the biological information acquisition system 200 is used for acquisition of an electrocardiogram waveform as one example. In FIGS. 14(a) to 14(c), the electrodes 30 at three positions selected by the electrode selector are hatched with positively-sloped lines.

First, in a state in which the subject lies on the sheet 400 to which the electrode sheet unit 150 is bonded, the electrode selector (controller 91) controls operation of the switcher 96.

More specifically, the electrode selector (controller 91) sequentially connects, by control of operation of the switcher 96, each electrode 30 and the switch 96*a* corresponding thereto one by one, thereby individually measuring the electrostatic capacitance. After completion of measurement of the electrostatic capacitance for all the electrodes 30 included in the electrode sheet unit 150, the controller 91 integrates the electrostatic capacitance data for all the electrodes 30, thereby generating the distribution of the electrostatic capacitance in the arrangement region 503 for the electrodes 30 as the image data shown in grayscale.

Then, from the generated image data, the electrode selector determines, using artificial intelligence, the posture of the biological body 300, i.e., the posture of the subject, as any of the left lateral decubitus position (see FIG. 13(*a*)), the supine position (see FIG. 13(*b*)), and the right lateral decubitus position (see FIG. 13(*c*)), for example.

Next, the electrode selector selects, by control of operation of the switcher 96, the electrodes at three positions 30 suitable for acquisition of an electrocardiogram waveform in the determined posture. At this point, as described above, as one example, the electrode selector selects the following: as the positive electrode 36, the electrode 30 having the maximum electrostatic capacitance from the electrodes 30 arranged at the positions corresponding to the lower portion of the upper body (or the portion below the lower portion of the upper body) of the biological body 300 and the left side of the biological body 300; as the negative electrode 37, the electrode 30 having the maximum electrostatic capacitance from the electrodes 30 arranged at the positions corresponding to the upper portion of the upper body of the biological body 300 and the right side of the biological body 300; and, as the ground electrode 38, the electrode 30 having the maximum electrostatic capacitance from the electrodes 30 arranged at the positions corresponding to the upper portion of the upper body of the biological body 300 and the left side of the biological body 300.

More specifically, in a case where the posture of the subject is determined as the left lateral decubitus position, the electrode selector selects, as one example, the electrodes 30 at three positions shown in FIG. 14(*a*) as the positive electrode 36, the negative electrode 37, and the ground electrode 38.

In a case where the posture of the subject is determined as the supine position, the electrode selector selects, as one example, the electrodes 30 at three positions shown in FIG. 14(*b*) as the positive electrode 36, the negative electrode 37, and the ground electrode 38.

In a case where the posture of the subject is determined as the right lateral decubitus position, the electrode selector selects, as one example, the electrodes 30 at three positions shown in FIG. 14(*c*) as the positive electrode 36, the negative electrode 37, and the ground electrode 38.

Then, the biological information acquirer (controller 91) performs induction equivalent to II induction with these electrodes 30 (positive electrode 36, negative electrode 37, and ground electrode 38) at three positions, thereby acquiring an electric signal. The electrocardiogram waveform detection circuit 95 generates electrocardiographic data (value) over time based on the electric signal, and inputs such data to the controller 91. The controller 91 displays, on the display, transition of the electrocardiographic data changing over time as an electrocardiogram waveform. In this manner, an electrocardiogram waveform can be acquired from the biological body 300.

Note that in the present invention, the biological information acquisition system 200 may be configured such that operation of the controller 91 is started according to input operation for an operator (not shown) of the terminal, or may be configured such that operation of the controller 91 is started taking, as a trigger, arrangement of the electrode sheet 100 along the biological body 300.

Moreover, in the present invention, the electrode selector may select, as each of the electrodes 30 (positive electrode 36, negative electrode 37, and ground electrode 38) at three positions, either one electrode 30 or a group of multiple electrodes 30 adjacent to each other.

Further, after determination of the posture of the biological body 300, i.e., the posture of the subject, from the generated image data with the artificial intelligence, the body joints (e.g., parts indicated by chain double-dashed lines 381 to 385 in FIGS. 13(*a*) to 13(*c*)) of the subject may be characterized as key points from the posture information, and the positive electrode 36, the negative electrode 37, and the ground electrode 38 may be selected based on such information.

Modification of Second-First Embodiment

Next, a modification of the first embodiment will be described using FIGS. 16(*a*) and 16(*b*). Note that FIG. 16(*b*) shows an enlarged view of a portion corresponding to a portion A shown in FIG. 16(*a*).

Figure 16:
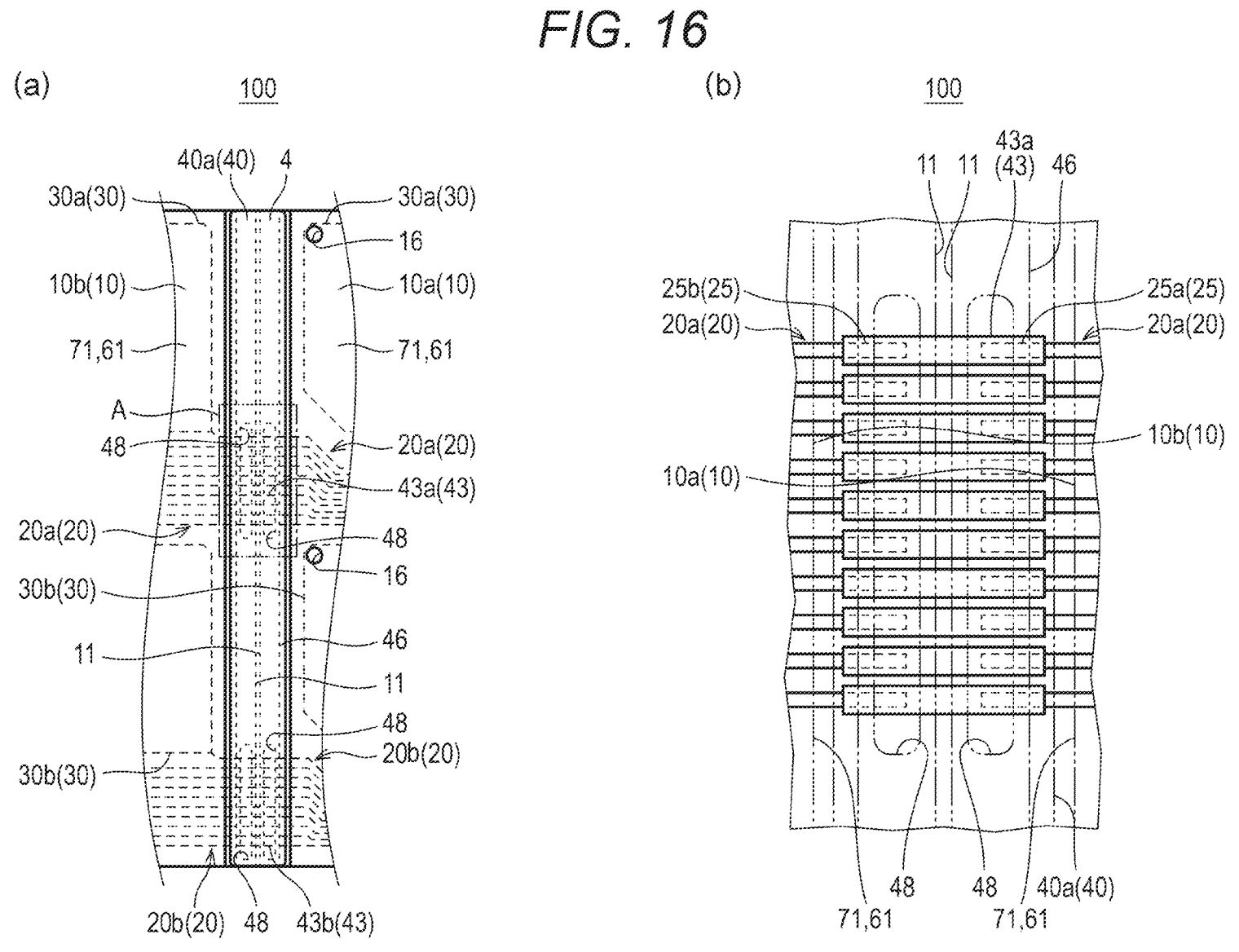

As shown in FIGS. 16(*a*) and 16(*b*), the electrode sheet 100 according to the present modification is different from the electrode sheet 100 according to the first embodiment in that the width of the stretchable junction line 43 is greater than the width of the stretchable line 20, and is similar to the electrode sheet 100 according to the first embodiment on the other points.

According to this configuration, when the stretchable junction lines 43 and the stretchable lines 20 are electrically connected to each other with the junction sheet 40 and the corresponding unit sheet 10 positioned relative to each other, even if the stretchable junction lines 43 and the corresponding unit sheet 10 are slightly shifted from each other in the Y-direction (direction of the width of the stretchable junction line 43), the stretchable junction lines 43 can be connected to the stretchable lines 20 by properly positioning the stretchable junction lines 43 relative to the stretchable lines 20.

Note that the stretchable junction line 43 may be formed with the same width as that of a portion of the stretchable line 20 connected to the stretchable junction line 43 or may be formed narrower than such a portion.

[Second Embodiment] Next, a second embodiment will be described using FIGS. 17 and 18. Note that FIGS. 17 and 18 show a cut surface of an electrode sheet 100 along a line corresponding to the C-C line of FIG. 1.

The electrode sheet 100 according to the present embodiment is different from the electrode sheet 100 according to the first embodiment in that no junction sheets 40 are provided and stretchable lines 20 of one unit sheet 10 and stretchable lines 20 of another unit sheet 10 are directly connected to each other, and is similar to the electrode sheet 100 according to the first embodiment on the other points.

With this configuration, a structure can also be achieved, in which the multiple unit sheets 10 are favorably connected to each other to integrally form the electrode sheet 100.

Figure 17:
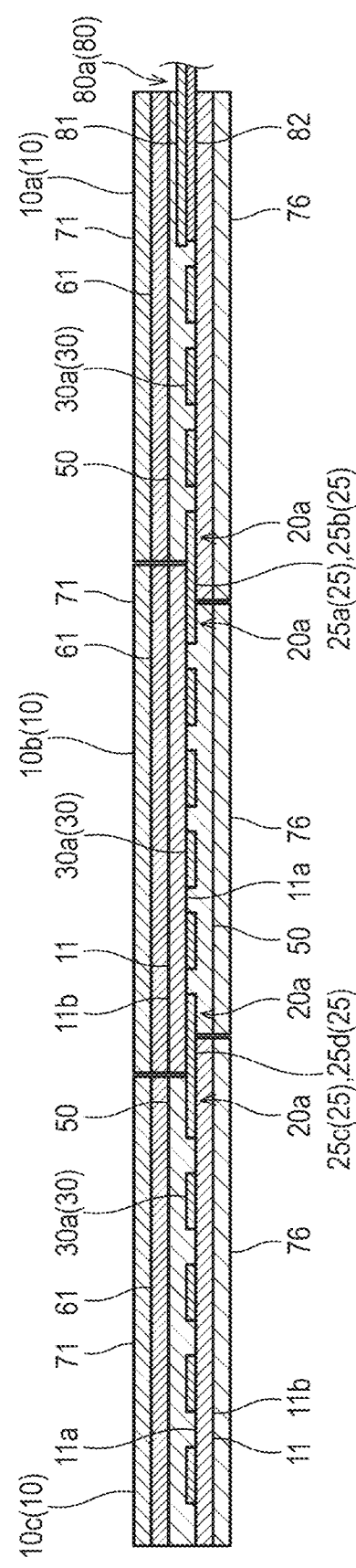
FIG. 17 is a schematic end view showing an electrode sheet according to a second embodiment.
Figure 18:
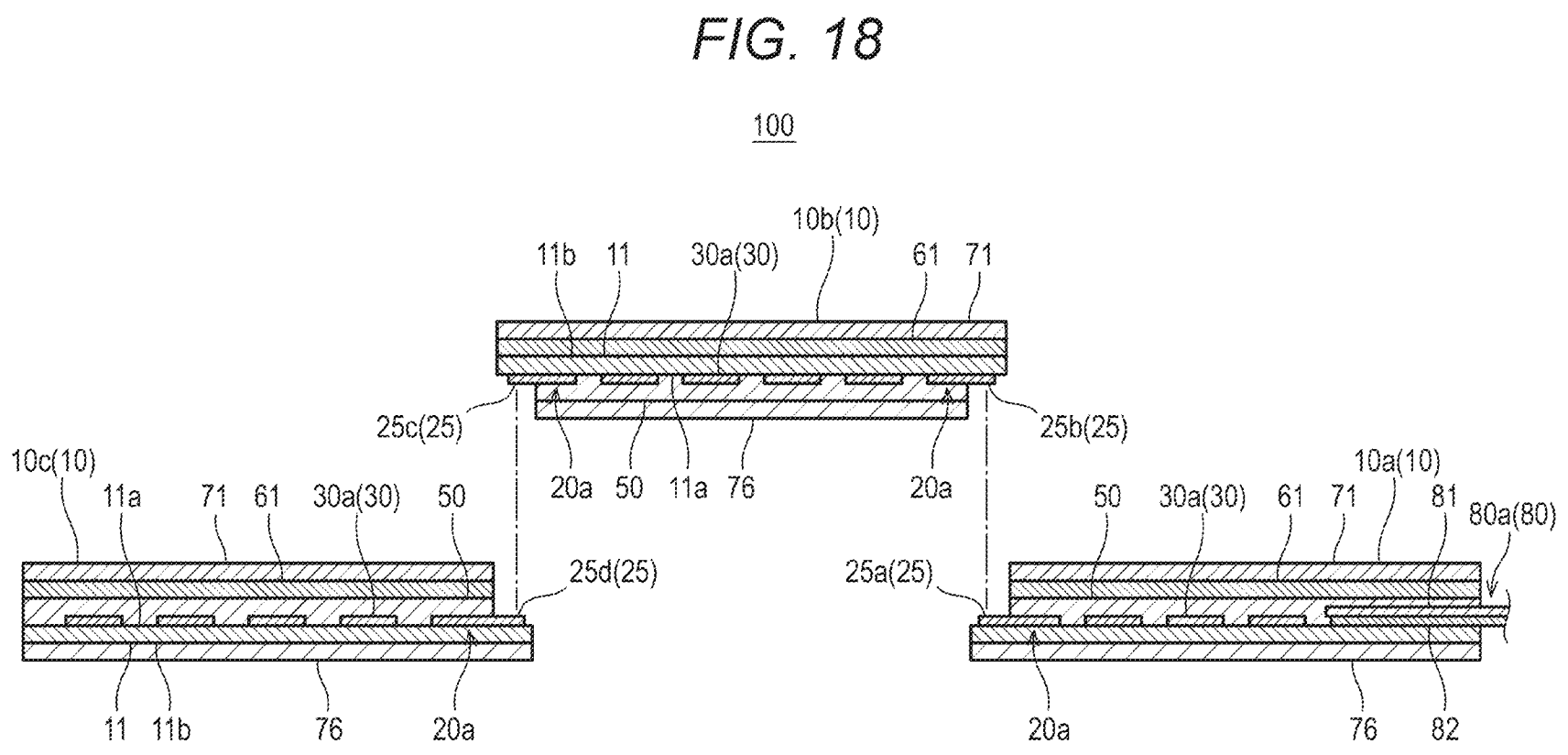

More specifically, as shown in FIGS. 17 and 18, in the case of the present embodiment, the stretchable lines 20 and multiple electrodes 30 are formed on the other surface 11*b* of a stretchable base 11 in a second unit sheet 10*b* arranged between a first unit sheet 10*a* and a third unit sheet 10*c*. Moreover, in the second unit sheet 10*b*, a stretchable cover 50 is arranged on the side close to the other surface 11*b* of the stretchable base 11. That is, in the second unit sheet 10*b*, arrangement of the stretchable base 11, the stretchable lines 20, the multiple electrodes 30, and the stretchable cover 50 is vertically inverted from arrangement of these layers in the first unit sheet 10*a* and the third unit sheet 10*c*. Second connection terminal portions 25*b* of the second unit sheet 10*b* are directly connected (e.g., fused) to first connection terminal portions 25*a* of the first unit sheet 10*a*, and third connection terminal portions 25*c* of the second unit sheet 10*b* are directly connected (e.g., fused) to fourth connection terminal portions 25*d* of the third unit sheet 10*c*. Note that the thicknesses of the stretchable base 11 and the stretchable cover 50 are preferably the same in the first unit sheet 10*a*, the second unit sheet 10*b*, and the third unit sheet 10*c* and the stretchable base 11 and the stretchable cover 50 with a thickness of 25 μm are applied thereto. With this configuration, even if arrangement in the first unit sheet 10*a* and the third unit sheet 10*c* and arrangement in the second unit sheet 10*b* are vertically inverted from each other, an insulating layer interposed between each sheet and a biological body 300 can have the same thickness. Thus, there is no adverse effect on an accuracy in determination of the posture of the biological body 300 and sensing of an electrocardiographic signal.

Each embodiment has been described above with reference to the drawings, but these embodiments are examples of the present invention and various configurations other than the above-described configurations can be employed.

For example, the example where the electrode sheet unit 150 is bonded to the sheet 400 upon use has been described above, but the electrode sheet unit 150 may be bonded, for example, to a comforter.

With this configuration, when an electrocardiogram waveform is acquired, the electrode sheet unit 150 is arranged on the chest side of the biological body 300 close to the heart thereof, and therefore, the stability and accuracy of the acquired electrocardiogram waveform can be improved.

The example where the biological information acquisition system 200 detects a change in the electrostatic capacitance to determine the posture of the biological body 300 has been described above, but the biological information acquisition system 200 may be configured, for example, to detect the presence or absence of excretion (urination or defecation) based on a change in the electrostatic capacitance at the lower body of the biological body 300 (e.g., person requiring care). In this case, during monitoring of the biological body 300, the biological information acquisition system 200 selects the electrodes 30 arranged at positions corresponding to the lower body of the biological body 300, and measures the electrostatic capacitance.

The example where the posture of the biological body 300 is determined (categorized), using the artificial intelligence, as any of the left lateral decubitus position, the supine position, and the right lateral decubitus position has been described above, but the type of posture determined (categorized) using the artificial intelligence is not limited to this example in the present invention and the artificial intelligence may be configured to more finely determine (categorize) the posture of the biological body 300.

The example where the biological information acquisition system 200 is used for acquisition of an electrocardiogram waveform has been described above, but the present invention is not limited to this example.

More specifically, the biological information acquisition system 200 may be used to measure the respiration or pulse of the biological body 300 simultaneously with acquisition of an electrocardiogram waveform or measure only the respiration or pulse of the biological body 300, for example.

The example where the electrode sheets 100 (electrode sheet unit 150) are bonded to the bedclothes has been described above, but the electrode sheets 100 may be bonded to a seat (backrest) of an automobile, for example. In this case, the biological information acquisition system 200 can determine the posture (whether or not in a proper seating state) of a driver, and can monitor the biological information such as the heart rate and respiration of the driver. In this case, drowsy driving can also be determined using the acquired biological information, for example.

The present embodiments include the following technical ideas.

(1) A biological information acquisition system including:
a flexible electrode sheet having multiple electrodes arranged in an array;
an electrode selector that acquires an electric parameter from the multiple electrodes in a state in which the electrode sheet is arranged along a biological body such that the multiple electrodes do not contact the biological body to select an electrode to be used for acquisition of biological information based on the acquired electric parameter; and
a biological information acquirer that acquires the biological information from the electrode selected by the electrode selector in a state in which the electrode sheet is arranged along the biological body such that the multiple electrodes do not contact the biological body.

(2) The biological information acquisition system according to (1), in which
the electrode selector selects, by determination using artificial intelligence, the electrode to be used for acquisition of the biological information.

(3) The biological information acquisition system according to (1) or (2), in which
the electrode selector detects a change in an electrostatic capacitance as the electric parameter, determines a posture of the biological body based on the detected change, and selects the electrode to be used for acquisition of the biological information based on a determination result of the posture.

(4) The biological information acquisition system according to any one of (1) to (3), in which
the electrode selector selects electrodes at three positions suitable for acquisition of an electrocardiogram waveform by a three-point induction method, and the biological information acquirer acquires, as the biological information, the electrocardiogram waveform acquired by the three-point induction method.

(5) The biological information acquisition system according to any one of (1) to (4), in which
the electrode sheet includes multiple unit sheets connected to each other,
each of the unit sheets has a stretchable base, multiple stretchable lines formed on the stretchable base and extending parallel with each other, and the multiple electrodes each formed at one end of two or more of the multiple stretchable lines, the multiple unit sheets are arranged in a direction of arrangement of the multiple electrodes, and of the stretchable lines of one of the unit sheets, the stretchable lines which do not end at the electrodes are each individually connected to the stretchable lines of another one of the unit sheets adjacent to the one of the unit sheets.

(6) The biological information acquisition system according to (5), in which the multiple unit sheets are connected to each other via junction sheets, each of the junction sheets has a stretchable junction base and multiple stretchable junction lines formed on the stretchable junction base and extending parallel with each other, and the stretchable lines of the one of the unit sheets and the stretchable lines of the another one of the unit sheets are connected to each other via the stretchable junction lines.

(7) An electrode sheet comprising:

multiple unit sheets connected to each other, in which each of the unit sheets has a stretchable base, multiple stretchable lines formed on the stretchable base and extending parallel with each other, and multiple electrodes each formed at one end of two or more of the stretchable lines, the multiple unit sheets are arranged in a direction of arrangement of the multiple electrodes, and of the stretchable lines of one of the unit sheets, the stretchable lines which do not end at the electrodes are each individually connected to the stretchable lines of another one of the unit sheets adjacent to the one of the unit sheets.

(8) The electrode sheet according to (7), in which a stretchable cover that covers the multiple stretchable lines is stacked and arranged on the stretchable base, and end portions of the multiple stretchable lines on a side close to an adjacent one of the unit sheets form connection terminal portions exposed through the stretchable cover.

(9) The electrode sheet according to (7) or (8), in which the multiple unit sheets are connected to each other via junction sheets, each of the junction sheet has a stretchable junction base and multiple stretchable junction lines formed on the stretchable junction base and extending parallel with each other, and the stretchable lines of the one of the unit sheets and the stretchable lines of the another one of the unit sheets are connected to each other via the stretchable junction lines.

(10) The electrode sheet according to (9), in which a width of each of the stretchable lines is greater than a width of each of the stretchable junction lines.

(11) The electrode sheet according to any one of (7) to (10), further comprising:

a bonding layer or an adhesive layer that bonds the electrode sheet to an attachment target.

(12) The electrode sheet according to any one of (7) to (11), in which an external connection terminal portion is provided at an end portion of one of the multiple unit sheets positioned at one end in a direction of arrangement of the multiple unit sheets, the end portion being positioned on a side opposite to the other unit sheets, the external connection terminal portion has a non-stretchable base, and a lead line formed on the non-stretchable base and connected to the stretchable lines, and part of the lead line forms an external connection terminal.

EXAMPLES

Hereinafter, Examples 1 to 3 and Comparative Examples 1 to 3 will be described using FIGS. 19(a) to 20(c).

In Examples 1 to 3 and Comparative Examples 1 to 3, the silhouette of a subject (biological body 300) was detected based on electrostatic capacitance distribution by means of a biological information acquisition system 200 according to the examples and a biological information acquisition system (not shown) according to the comparative examples.

The biological information acquisition system according to Examples 1 to 3 is the biological information acquisition system 200 described above in the first embodiment.

The biological information acquisition system according to Comparative Examples 1 to 3 is different from the biological information acquisition system 200 according to Examples 1 to 3 in that a board having multiple electrodes 30 is provided instead of an electrode sheet 100 as in Non-Patent Literature 1, and is similar to the biological information acquisition system 200 according to Examples 1 to 3 on the other points.

FIGS. 19(a) to 20(c) are image data obtained using the biological information acquisition system 200 (or the biological information acquisition system according to the comparative examples) and indicating the distribution of the electrostatic capacitance accumulated in each electrode 30. As described above, on the generated image, a portion corresponding to the biological body 300 has a higher brightness (more whitened), and a portion not corresponding to the biological body 300 has a lower brightness (more blackened).

FIG. 19(a) shows the image data in Example 1, FIG. 19(b) shows the image data in Example 2, and FIG. 19(c) shows the image data in Example 3. FIG. 20(a) shows the image data in Comparative Example 1, FIG. 20(b) shows the image data in Comparative Example 2, and FIG. 20(c) shows the image data in Comparative Example 3.

In Example 1 and Comparative Example 1, the electrostatic capacitance accumulated in each electrode 30 was measured in a state in which the posture of the subject is a left lateral decubitus position (see FIG. 13(a) of the first embodiment).

In Example 2 and Comparative Example 2, the electrostatic capacitance accumulated in each electrode 30 was measured in a state in which the posture of the subject is a supine position (see FIG. 13(b) of the first embodiment).

In Example 3 and Comparative Example 3, the electrostatic capacitance accumulated in each electrode 30 was measured in a state in which the posture of the subject is a right lateral decubitus position (see FIG. 13(c) of the first embodiment).

As shown in FIG. 19(a), in Example 1, both legs (legs 330) of the biological body 300 are viewable as a silhouette. On the other hand, as shown in FIG. 20(a), in Comparative Example 1, the left leg (leg positioned on the near side in FIG. 20(a) of both legs (legs 330) of the biological body 300 is mainly viewable as a silhouette, and the shape of the right leg (leg positioned on the far side in FIG. 20(a)) is not clear as a silhouette.

Figure 19:
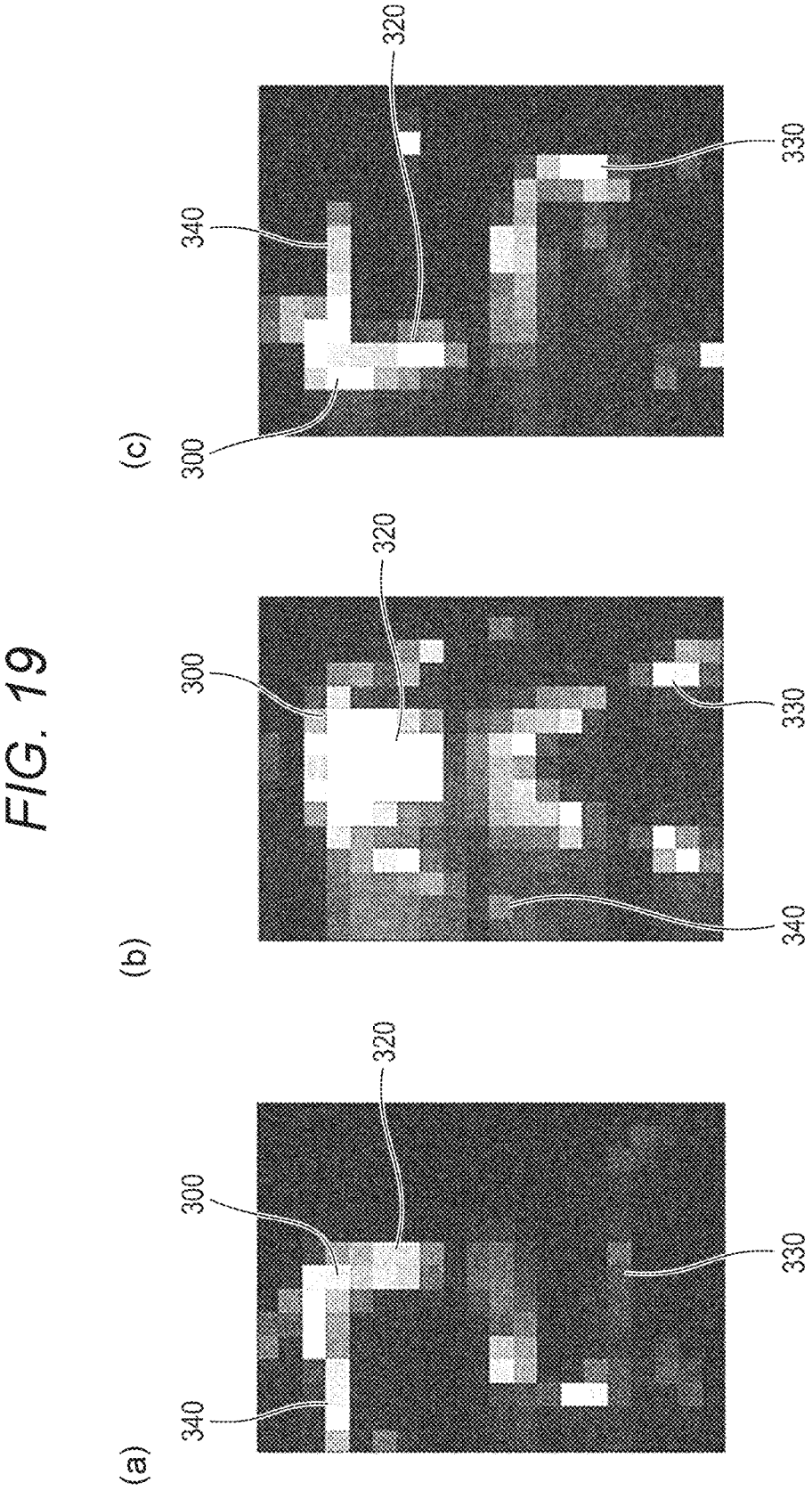
FIGS. 19(*a*), 19(*b*), and 19(*c*) are image data indicating, in grayscale, electrostatic capacitance distribution in Examples 1 to 3.
Figure 20:
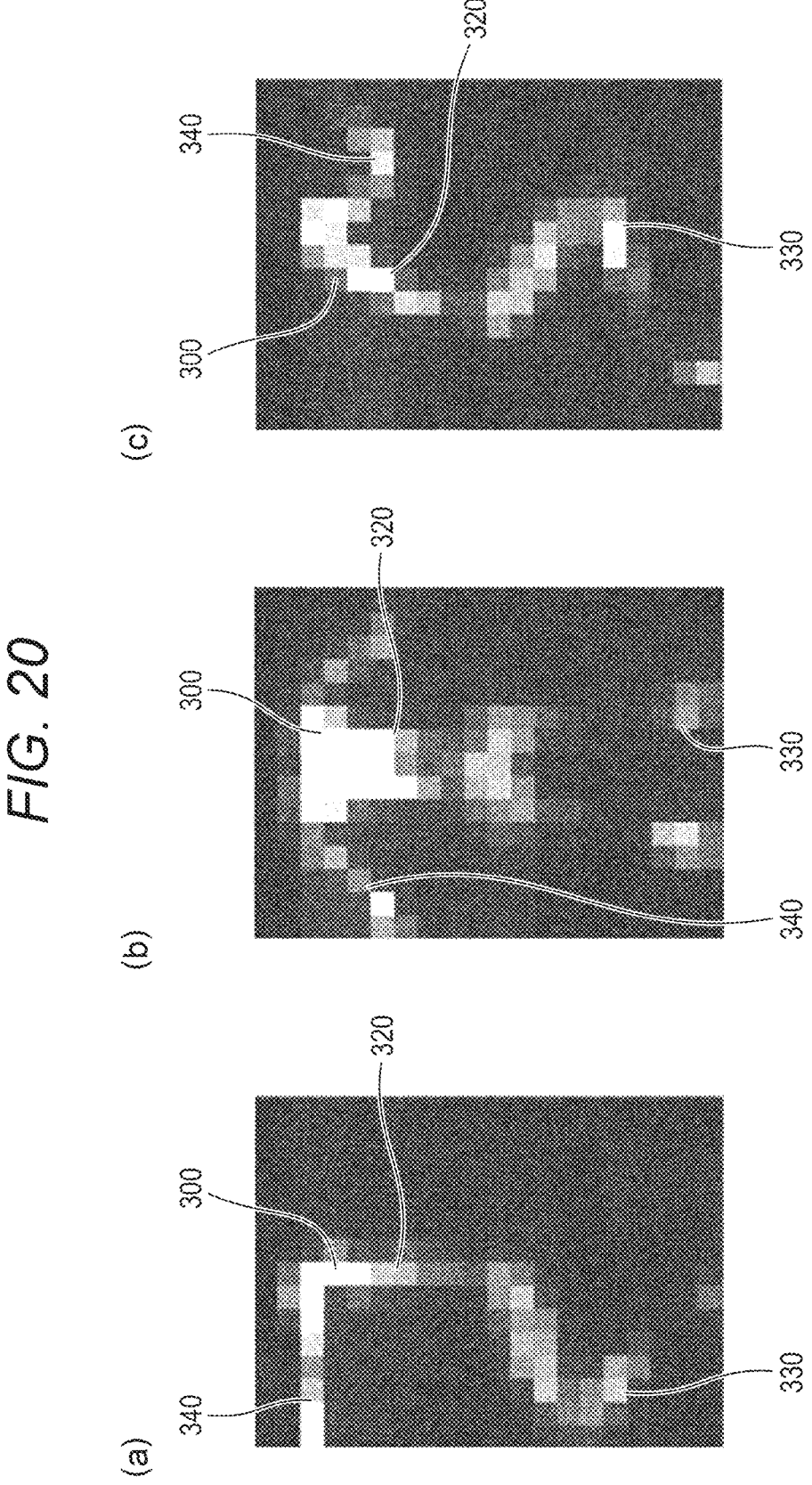
FIGS. 20(*a*), 20(*b*), and 20(*c*) are image data indicating, in grayscale, electrostatic capacitance distribution in Comparative Examples 1 to 3.

As shown in FIG. 19(b), in Example 2, each part (trunk 320, legs 330, and arms 340) of the biological body 300 is more clearly viewable as a silhouette as compared to Comparative Example 2 shown in FIG. 20(*b*).

As shown in FIG. 19(*c*), in Example 3, both legs (legs 330) of the biological body 300 are viewable as a silhouette. On the other hand, as shown in FIG. 20(*c*), in Comparative Example 3, the right leg (leg positioned on the near side in FIG. 20(*c*)) is mainly viewable as a silhouette, and the shape of the left leg (leg positioned on the far side in FIG. 20(*c*)) is not clear as a silhouette.

As described above, according to the biological information acquisition system 200 of the first embodiment, the posture of the biological body 300 can be more accurately detected.

Next, Example 4 will be described using FIG. 21.

In Example 4, a subject slept 30 nights on a sheet 400 to which an electrode sheet unit 150 is bonded, and the resistance value of a stretchable line 20 was measured in every night. Note that a sleep time per night was about seven hours. After a lapse of the 30 nights, the sheet 400 to which the electrode sheet unit 150 is bonded was washed and dried (dried with air), and the resistance value of the stretchable line 20 was further measured. Note that the electrode sheet unit 150 used in Example 4 included six electrode sheets 100 as one example.

Note that the resistance values of ones, which are formed with electrodes 30, of the multiple stretchable lines 20 were measured.

Figure 21:
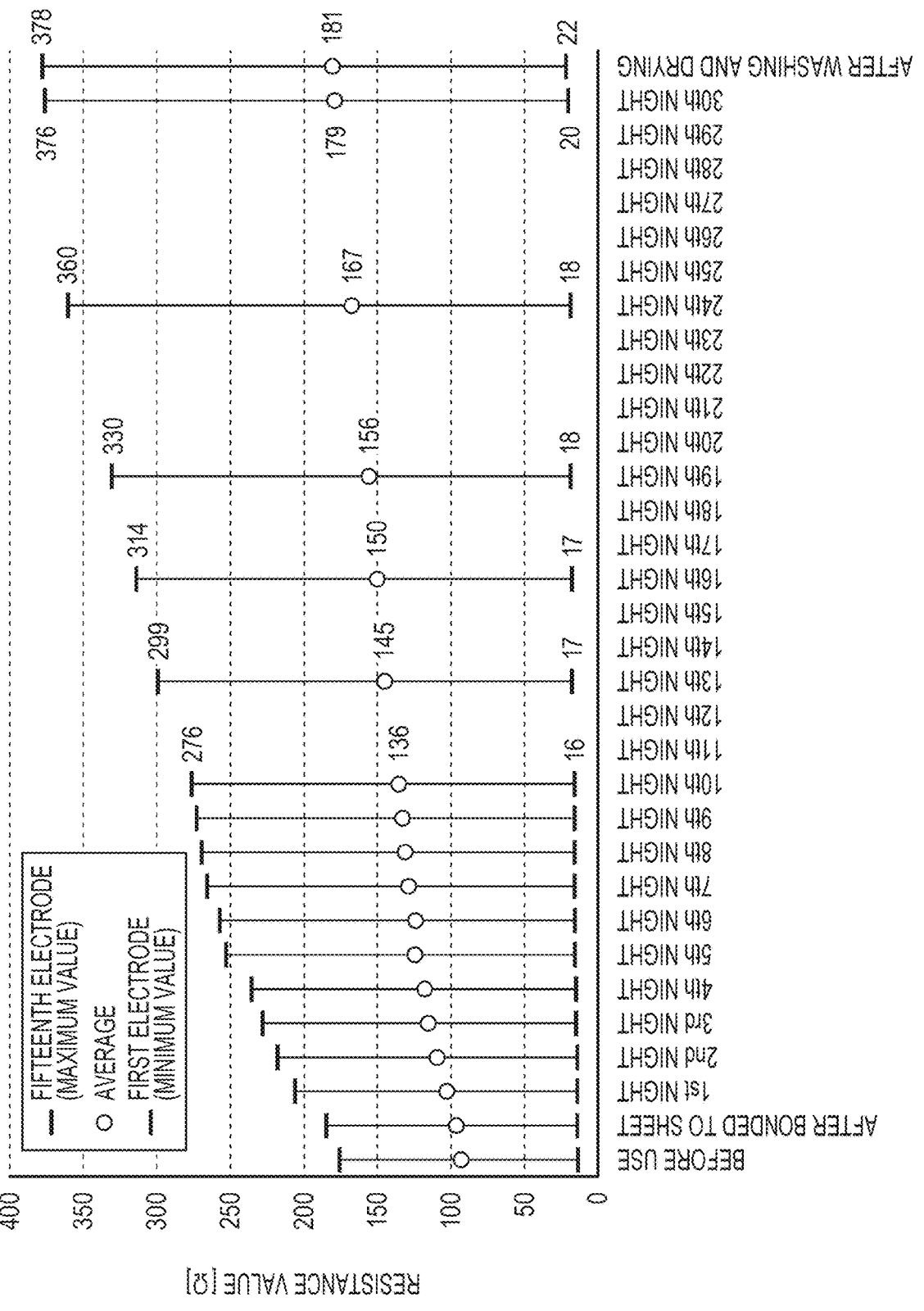
FIG. 21 is a graph showing a change in a resistance value of a stretchable line in Example 4.

FIG. 21 is a graph showing a change in the resistance value of the stretchable line 20 in a case where the electrode sheet unit 150 is bonded to the sheet 400 and practical use thereof is repeated including sleep of the subject, the horizontal axis indicating the time and the left vertical axis indicating the resistance value ($\Omega$).

In the electrode sheet 100, 15 electrodes 30 arranged in the X-direction will be referred to as first to fifteenth electrodes in this order from the side (e.g., right side) on which an external connection terminal portion 80 is provided.

The graph shown in FIG. 21 shows the resistance value of the stretchable line 20 corresponding to the first electrode (electrode 30 arranged closest to the external connection terminal portion 80) of the first to fifteenth electrodes, the resistance value of the stretchable line 20 corresponding to the fifteenth electrode (electrode 30 arranged closest to the side opposite to the external connection terminal portion 80), and the average of the resistance values of the stretchable lines 20 corresponding to the first to fifteenth electrodes. In the electrode sheet 100, the resistance value of the stretchable line 20 decreases as the electrode 30 is positioned closer to the external connection terminal portion 80, and increases as the electrode 30 is positioned farther from the external connection terminal portion 80. Thus, the resistance value of the first electrode is the minimum resistance value of the stretchable line 20, and the resistance value of the fifteenth electrode is the maximum resistance value of the stretchable line 20.

As shown in FIG. 21, the resistance value of the stretchable line 20 after a lapse of the 30 nights was 400$\Omega$ or less in terms of any of the minimum value (resistance value of the first electrode) the maximum value (resistance value of the fifteenth electrode), and the average. Moreover, also in the washed and dried electrode sheet 100, the resistance value of the stretchable line 20 was 400$\Omega$ or less in terms of any of the minimum value (resistance value of the first electrode), the maximum value (resistance value of the fifteenth electrode), and the average.

These results show that even if the practical use, which includes sleep and washing of the electrode sheet unit 150 (multiple electrode sheets 100) is repeated for a certain period, the resistance value of the stretchable line 20 greatly falls below 2 k$\Omega$.

The biological information acquisition system 200 according to the present invention detects a change in the electrostatic capacitance under an extremely-high impedance. Thus, according to study conducted by the present inventors, the biological information acquisition system 200 can accept a resistance value of up to about 2 k$\Omega$ as the resistance value of the stretchable line 20. Consequently, the biological information acquisition system 200 of the present invention is assumed to favorably maintain the performance of the electrode sheet 100 even in the practical use including sleep and washing.

LIST OF REFERENCE SIGNS

10 Unit Sheet
10*a* First Unit Sheet
10*b* Second Unit Sheet
10*c* Third Unit Sheet
11 Stretchable Base
11*a* One Surface
11*b* Other Surface
16 Through-Hole
20 Stretchable Line
20*a* First Stretchable Line
20*b* Second Stretchable Line
25 Connection Terminal Portion
25*a* First Connection Terminal Portion
25*b* Second Connection Terminal Portion
25*c* Third Connection Terminal Portion
25*d* Fourth Connection Terminal Portion
30 Electrode
30*a* First Electrode
30*b* Second Electrode
32 Cutout-Shaped Portion
36 Positive Electrode
37 Negative Electrode
38 Ground Electrode
40 Junction Sheet
40*a* First Junction Sheet
40*b* Second Junction Sheet
41 Stretchable Junction Base
43 Stretchable Junction Line
43*a* First Stretchable Junction Line
43*b* Second Stretchable Junction Line
46 Stretchable Junction Cover
48 Opening
48*a* First Opening
48*b* Second Opening
50 Stretchable Cover
50*a* One Surface
50*b* Other Surface
61 Bonding Layer
71 First Release Film
76 Second Release Film
80 External Connection Terminal Portion
80*a* First External Connection Terminal Portion
80*b* Second External Connection Terminal Portion
81 Non-Stretchable Base
82 Lead Line
83 External Connection Terminal
91 Controller
94 Electrostatic Capacitance Detection Circuit 95 Electrocardiogram Waveform Detection Circuit
96 Switcher
96a Switch
100 Electrode Sheet
100a One Surface
100b Other Surface
150 Electrode Sheet Unit
200 Biological Information Acquisition System
300 Biological Body
310 Head
320 Trunk
330 Leg
340 Arm
350 Insulator
360 Skin
370 Capacitor
381 to 385 Chain Double-Dashed Lines
400 Sheet (Attachment Target)
450 Bed
501, 502 Virtual Line
503 Arrangement Region

The invention claimed is:

1. A biological information acquisition system comprising:
  a flexible electrode sheet having multiple electrodes arranged in an array, wherein the electrode sheet includes multiple unit sheets connected to each other,
  each of the unit sheets has a stretchable base, multiple stretchable lines formed on the stretchable base and extending parallel with each other, and the multiple electrodes each formed at one end of two or more of the multiple stretchable lines,
  the multiple unit sheets are arranged in a direction of arrangement of the multiple electrodes,
  of the stretchable lines of one of the unit sheets, the stretchable lines which do not end at the electrodes are each individually connected to the stretchable lines of another one of the unit sheets adjacent to the one of the unit sheets,
  the multiple unit sheets are connected to each other via junction sheets,
  each of the junction sheets has a stretchable junction base, multiple stretchable junction lines formed on the stretchable junction base and extending parallel with each other, and a stretchable junction cover formed on the stretchable junction lines, and
the stretchable lines of the one of the unit sheets and the stretchable lines of the another one of the unit sheets are connected to each other via the stretchable junction lines, via an opening formed in the stretchable junction cover;
  an electrode selector that acquires an electric parameter from the multiple electrodes to determine which electrodes of the multiple electrodes are not in contact with a biological body and selects electrodes of the multiple electrodes adapted to be in contact with the biological body for acquisition of biological information based on the acquired electric parameter; and
  a biological information acquirer that acquires the biological information from the electrodes of the multiple electrodes selected by the electrode selector.

2. The biological information acquisition system according to claim 1, wherein
  the electrode selector selects the electrodes of the multiple electrodes, by using artificial intelligence.

3. The biological information acquisition system according to claim 1, wherein the electrode selector detects a change in an electrostatic capacitance as the electric parameter, determines a posture of the biological body based on the detected change, and selects the electrodes of the multiple electrodes to be used for acquisition of the biological information based on a determination result of the posture.

4. The biological information acquisition system according to claim 1, wherein
  the electrodes of the multiple electrodes selected by the electrode selector are along three positions suitable for acquisition of an electrocardiogram waveform, and the biological information acquirer acquires, as the biological information, the electrocardiogram waveform by the electrodes of the multiple electrodes along the three positions.

5. An electrode sheet comprising:
  multiple unit sheets connected to each other,
  wherein each of the unit sheets has a stretchable base, multiple stretchable lines formed on the stretchable base and extending parallel with each other, and multiple electrodes each formed at one end of two or more of the stretchable lines,
  the multiple unit sheets are arranged in a direction of arrangement of the multiple electrodes, and
  of the stretchable lines of one of the unit sheets, the stretchable lines which do not end at the electrodes are each individually connected to the stretchable lines of another one of the unit sheets adjacent to the one of the unit sheets,
  the multiple unit sheets are connected to each other via junction sheets,
  each of the junction sheets has a stretchable junction base, multiple stretchable junction lines formed on the stretchable junction base and extending parallel with each other, and a stretchable junction cover formed on the stretchable junction lines, and
  the stretchable lines of the one of the unit sheets and the stretchable lines of the another one of the unit sheets are connected to each other via the stretchable junction lines, via an opening formed in the stretchable junction cover.

6. The electrode sheet according to claim 5, wherein
  a stretchable cover that covers the multiple stretchable lines is stacked and arranged on the stretchable base, and
  end portions of the multiple stretchable lines on a side close to an adjacent one of the unit sheets form connection terminal portions exposed through the stretchable cover.

7. The electrode sheet according to claim 5, wherein
  a width of each of the stretchable lines is greater than a width of each of the stretchable junction lines.

8. The electrode sheet according to claim 5, further comprising:
  a bonding layer or an adhesive layer that bonds the electrode sheet to an attachment target.

9. The electrode sheet according to claim 5, wherein
  an external connection terminal portion is provided at an end portion of one of the multiple unit sheets positioned at one end in a direction of arrangement of the multiple unit sheets, the end portion being positioned on a side opposite to the other unit sheets,
  the external connection terminal portion has
  a non-stretchable base, and
  a lead line formed on the non-stretchable base and connected to the stretchable lines, and part of the lead line forms an external connection termi-
nal.

\* \* \* \* \*